United States Patent
King et al.

(10) Patent No.: US 6,197,932 B1
(45) Date of Patent: Mar. 6, 2001

(54) MODULATORS OF ACTIN

(75) Inventors: Mary-Claire King; Eric D. Lynch, both of Seattle; Ming K. Lee, Bothell; Jan E. Morrow; Piri L. Welcsh, both of Seattle, all of WA (US); Pedro E. Leon, San Jose (CR)

(73) Assignees: The University of Washington, Seattle, WA (US); The University of Costa Rica, San Jose (CR)

( * ) Notice: Subject to any disclaimer, the term of this patent is extended or adjusted under 35 U.S.C. 154(b) by 0 days.

(21) Appl. No.: 09/323,735

(22) Filed: Jun. 1, 1999

Related U.S. Application Data

(62) Division of application No. 09/080,897, filed on May 18, 1998, now Pat. No. 5,985,574
(60) Provisional application No. 60/063,737, filed on Oct. 29, 1997.

(51) Int. Cl.[7] .............................. C07K 1/00; A61K 69/00; G01N 33/00
(52) U.S. Cl. ..................... 530/350; 424/185.1; 436/86
(58) Field of Search ................. 435/69.1; 424/185.1; 530/350; 436/86

(56) References Cited

PUBLICATIONS

Watanabe et al., EMBO J., 16, 3044–3056, Jun. 1997.*

* cited by examiner

Primary Examiner—Rebecca F. Prouty
Assistant Examiner—M. Monshipouri
(74) Attorney, Agent, or Firm—Richard Aron Osman

(57) ABSTRACT

The invention provides methods and compositions which find use, inter alia, for modulating the stabilization of actin filaments. The compositions may comprise one or more polypeptide moieties derived from a novel human diaphanous polypeptide and/or one or more nucleic acid moieties derived from a novel human diaphanous gene or gene transcript. The invention also provides agents which specifically modify the binding of a natural human diaphanous gene or gene product with a natural binding target thereof, isolated human diaphanous hybridization probes and primers capable of specifically hybridizing with the disclosed human diaphanous genes, human diaphanous-specific binding agents such as specific antibodies, and methods of making and using the subject compositions in diagnosis, therapy and in the biopharmaceutical industry.

19 Claims, No Drawings

MODULATORS OF ACTIN

CROSS-REFERENCE TO RELATED APPLICATION

This application is a divisional application of and claims priority to Ser. No. 09/080,897, filed May 18, 1998 now U.S. Pat. No. 5,985,574, which is a continuing application of and claims priority under 35USC120 to U.S. application Ser. No. 60/063,737, filed on Oct. 29, 1997.

The research carried out in the subject application was supported in part by NIH grant R01-DC01076. The government may have rights in any patent issuing on this application.

INTRODUCTION

1. Field of the Invention

The invention relates to a class of polypeptides involved in actin stabilization.

2. Background of the Invention

The actin cytoskeleton plays a central role in defining cellular structure and effecting dynamic changes in morphology. By selectively stabilizing and destabilizing actin polymerization, the cell is able to effect a wide range of structural reorganization and effect phenomena such as cell motility, phagocytosis, cytokinesis, mitosis, etc. Because these phenomenon are involved in myriad medically significant physiologies and pathologies, e.g. the progress of many pathogenic infections, invasion and metastisis of neoplasia, fertilization, clotting and wound repair, etc., the stability of actin polymerization is a choice target for therapuetic intervention. In fact, potent a drugs effecting actin filament destabilization and stabilization such as fungal-derived alkaloids including the cytochalasins and phalloidins are well known. Here we disclose a new family of modulators of actin polymer stabilization derived from a novel human diaphanous protein and gene.

Relevant Literature

Lynch ED, et al. (1997) Science 278(5341): 1315–1318 disclose nonsyndromic deafness DFNA1 associated with mutation of a human homolog of the Drosophila gene diaphanous. Watanabe N, et al. (1997) EMBO J 16:3044–3056, disclose a mouse gene with sequence similarity to the disclosed human gene. Bione S, et al. (1998) Am J Hum Genet 62(3): 533–541, report that a human homologue of the Drosophila melanogaster diaphanous gene is disrupted in premature ovarian failure. Vahava O, et al. (1998) Science 279(5358): 1950–1954. Mutation in transcription factor POU4F3 associated with inherited progressive hearing loss in humans.

SUMMARY OF THE INVENTION

The invention provides methods and compositions which find use, inter alia, for modulating the stabilization of actin filaments. The compositions may comprise one or more polypeptide moieties derived from a novel human diaphanous polypeptide and/or one or more nucleic acid moieties derived from a novel human diaphanous gene or gene transcript. The invention also provides agents which specifically modif the binding of a natural human diaphanous gene or gene product with a natural binding target thereof. Polypeptide components of subject compositions provide human diaphanous-specific structure and activity and may be produced recombinantly from transformed host cells from the subject human diaphanous polypeptide encoding nucleic acids. The invention provides isolated human diaphanous hybridization probes and primers capable of specifically hybridizing with the disclosed human diaphanous genes, human diaphanous-specific binding agents such as specific antibodies, and methods of making and using the subject compositions in diagnosis (e.g. genetic hybridization screens for human diaphanous transcripts), therapy (e.g. modulating a cellular function such as auditory signal transduction by introducing into the cell a subject modulator) and in the biopharmaceutical industry (e.g. as immunogens, reagents for isolating additional natural human diaphanous genes and alleles, reagents for screening bio/chemical libraries for ligands and lead and/or pharmacologically active agents, etc.).

DESCRIPTION OF PARTICULAR EMBODIMENTS OF THE INVENTION

In one embodiment, the modulators of the invention comprise a human diaphanous polypeptide (a plurality of amino acids linearly joined through peptide bonds) having a natural human diaphanous polypeptide-specific sequence and bioactivity (i.e. distinguished from natural murine and drosophila diaphanous sequences and bioactivities). SEQ ID NO: 1 depicts an exemplary natural cDNA encoding a human diaphanous polypeptide and SEQ ID NO: 2 depicts the corresponding encoded natural human diaphanous polypeptide. The subject polypeptides comprise at least a 6, preferably at least a 12, more preferably at least a 18, most preferably at least a 24 residue domain of SEQ ID NO:2, not found in natural mouse or drosophila diaphanous polypeptides. Human specific sequences are readily identified by aligning the respectivel sequences. In a particular embodiment, the subject polypeptides comprise at least a 36, preferably at least a 72, more preferably at least a 144, most preferably at least a 288 residue domain of SEQ ID NO:2.

The polypeptides provide natural human diaphanous polypeptide specific bioactivity or function, such as specific ligand binding or binding inhibition, antigenicity, immunogenicity, etc. Human diaphanous polypeptide-specific activity or function may be determined by convenient in vitro, cell-based, or in vivo assays: e.g. in vitro binding assays, cell culture assays, in animals (e.g. gene therapy, transgenics, etc.), etc. Binding assays encompass any assay where the molecular interaction of a human diaphanous polypeptide with a binding target is evaluated. The binding target may be a natural intracellular binding target such as a human diaphanous polypeptide regulating protein, effector or other regulator that directly modulates a human diaphanous polypeptide activity or its localization; or non-natural binding target such a specific immune protein such as an antibody, or an human diaphanous polypeptide specific agent such as those identified in bio/chemical screening assays. Exemplary binding targets include human prolifin and Rho polypeptides. Human diaphanous polypeptide-binding specificity may assayed by functional assays described below, binding equilibrium constants (usually at least about $10^7$ $M^{-1}$, preferably at least about $10^8$ $M^{-1}$, more preferably at least about $10^9$ $M^{-1}$), by the ability of the subject polypeptides to function as negative mutants in a human diaphanous polypeptide-expressing cells, to elicit a human diaphanous polypeptide specific antibody in a heterologous host (e.g. a rodent or rabbit), etc. The human diaphanous polypeptide binding specificity of the human diaphanous polypeptides necessarily distinguishes that of natural murine and drosophila homologs. In a particular embodiment, the sequence and function also distinguishes those of the natural human diaphanous 2 polypeptide.

In particular embodiments, modulators comprising human diaphanous polypeptides are isolated, pure or recombinant: an "isolated" polypeptide is unaccompanied by at least some of the material with which it is associated in its natural state, preferably constituting at least about 0.5%, and more preferably at least about 5% by weight of the total polypeptide in a given sample and a pure polypeptide constitutes at least about 90%, and preferably at least about 99% by weight of the total polypeptide in a given sample. A recombinant polypeptide comprises a non-natural terminus residue or is joined to other than an amino acid which it is joined to in a natural polypeptide. The polypeptides may be synthesized, produced by recombinant technology, or purified from cells. A wide variety of molecular and biochemical methods are available for biochemical synthesis, molecular expression and purification of the subject compositions, see e.g.

Molecular Cloning, A Laboratory Manual (Sambrook, et al. Cold Spring Harbor Laboratory), Current Protocols in Molecular Biology (Eds. Ausubel, et al., Greene Publ. Assoc., Wiley-Interscience, NY) or that are otherwise known in the art. Material and methods for the expression of heterologous recombinant polypeptides in bacterial cells (e.g. *E. coli*), yeast (e.g. *S. Cerevisiae*), animal cells (e.g. CHO, 3T3, BHK, baculovirus-compatible insect cells, etc.). The polypeptides may be provided uncomplexed with other moieties including other polypeptide moieties, complexed in a wide variety of covalent and/or non-covalent associations and binding complexes, etc., which may provide enhanced activity, stability, availability, targeting, etc.

Exemplary active modulators comprising human diaphanous polypeptides moieties include (using N→C nomenclature convention):

hDia1-del-1: MRG—residues 121–151 of SEQ ID NO:2 fusion polypeptide
hDia1-del-2: GFP—residues 197–205 of SEQ ID NO:2 fusion polypeptide
hDia1-del-3: FLAGG—residues 350–382 of SEQ ID NO:2 fusion polypeptide
hDia1-del-4: CYCLIN A—residues 439454 of SEQ ID NO:2 fusion polypeptide
hDia1-del-5: CYCLIN B1—residues 515–524 of SEQ ID NO:2 fusion polypeptide
hDia1-del-6: CYCLIN B2—residues 551–569 of SEQ ID NO:2 fusion polypeptide
hDia1-del-7: CYCLIN B3—residues 590–610 of SEQ ID NO:2 fusion polypeptide
hDia1-del-8: SH2—residues 611–630 of SEQ ID NO: 2 fusion polypeptide
hDia1-del-9: SH3—residues 651–670 of SEQ ID NO: 2 fusion polypeptide
hDia1-del-10: MRG—residues 674–773 of SEQ ID NO:2 fusion polypeptide
hDia1-del-11: GFP—residues 740–840 of SEQ ID NO:2 fusion polypeptide
hDia1-del-12: FLAGG—residues 841–940 of SEQ ID NO:2 fusion polypeptide
hDia1-del-13: CYCLIN A—residues 941–1040 of SEQ ID NO:2 fusion polypeptide
hDia1-del-14: CYCLIN B1—residues 1041–1140 of SEQ ID NO:2 fusion polypeptide
hDia1-del-15: CYCLIN B2—residues 1141–1171 of SEQ ID NO:2 fusion polypeptide The invention provides methods and compositions of selectively modulating cytoskeletal de/stabilization and/or the effective concentration of a human diaphanous protein within a target cell. The general methods involve introducing into the target cell an effective amount of a subject modulator, sufficient to selectively modulate actin cytoskeletal function of a cell. As demonstrated herein, the invention encompasses a wide variety of suitable methods of introduction, amounts, and modulator compositions, which are readily optimized empirically. In addition to the human diaphanous polypeptide moiety, the modulator may comprise a wide variety of additional moieties, including moieties which provide for detection, targeting, stability, proteolytic resistance, etc. Preferred modulators demonstrate cytoskelatal de/stabilization with several alternative methods of introduction, including direct medium uptake, uptake facilitated by chaotropic agents including detergents (e.g. TWEEN20, etc.), guanadine salts, etc., pulsed electric field, liposome fusion, etc.

The compositions may be advantageously combined and/or used in combination with other therapeutic or prophylactic agents, different from the subject compounds. In many instances, administration in conjunction with the subject compositions enhances the efficacy of such agents, see e.g. *Goodman & Gilman's The Pharmacological Basis of Therapeutics*, $9^{th}$ Ed., 1996, McGraw-Hill. In particular embodiments, such as where the modulators are polypeptides, the modulators may also be introduced indirectly by expression within the targeted cell. Such expression may be effected at least in part by transiently transfecting or by upregulation of a stably introduced polypeptide-encoding gene. A wide variety of well-established methods are known in the art for facilitating introduction, expression and/or stable integration of exogenous genes in targeted host cells (below).

The invention provides binding agents specific to the claimed modulators, including substrates, agonists, antagonists, natural intracellular binding targets, etc., methods of identifying and making such agents, and their use in diagnosis, therapy and pharmaceutical development. For example, novel polypeptide-specific binding agents include human diaphanous polypeptide—specific receptors, such as somatically recombined polypeptide receptors like specific antibodies or T-cell antigen receptors (see, e.g Harlow and Lane (1988) Antibodies, A Laboratory Manual, Cold Spring Harbor Laboratory) and other natural intracellular binding agents identified with assays such as one-, two- and three-hybrid screens, non-natural intracellular binding agents identified in screens of chemical libraries, etc. For diagnostic uses, such binding agents are frequently labeled, such as with fluorescent, radioactive, chemiluminescent, or other easily detectable molecules, either conjugated directly to the binding agent or conjugated to a probe specific for the binding agent. Agents of particular interest modulate human diaphanous polypeptide function, e.g. human diaphanous polypeptide-dependent actin de/stabilization.

The invention also provides efficient methods of identifying agents active at the level of a human diaphanous modulatable cellular function. Generally, these screening methods involve assaying for compounds which modulate a human diaphanous polypeptide interaction with a natural human diaphanous polypeptide binding target, etc. A wide variety of assays for binding agents are provided including labeled in vitro protein-protein binding assays, immunoassays, cell based assays, etc. The methods are amenable to automated, cost-effective high throughput screening of chemical libraries for lead compounds. Agents that modulate the interactions of a human diaphanous polypeptide with its ligands/natural binding targets can be used to modulate biological processes associated a human diaphanous polypeptide function, e.g. by contacting a cell comprising a human diaphanous polypeptide (e.g. administering to a subject comprising such a cell) with such an agent. Biological processes mediated by human diaphanous polypeptides include a wide variety of cellular events which are mediated when a human diaphanous polypeptide binds a ligand e.g. cytoskeletal modifications.

The amino acid sequences of the subject polypeptides are used to back-translate polypeptide-encoding nucleic acids optimized for selected expression systems (Holler et al. (1993) Gene 136, 323–328; Martin et al. (1995) Gene 154, 150–166) or used to generate degenerate oligonucleotide primers and probes for use in the isolation of natural human diaphanous polypeptide-encoding nucleic acid sequences ("GCG" software, Genetics Computer Group, Inc, Madison Wis.). Modulator polypeptide-encoding nucleic acids are used in polypeptide-expression vectors and incorporated into recombinant host cells, e.g. for expression and screening, e.g. for functional studies such as the efficacy of candidate agents to manipulate modulator polypeptide-modulated cell function, etc.

The invention also provides human diaphanous nucleic acids including hybridization probes and replication/amplification primers having a human diaphanous cDNA specific sequence comprising a fragment of a strand of SEQ ID NO: 1 sufficient to effect specific hybridization to the complementary strand of SEQ ID NO: 1 (i.e. specifically hybridize with a nucleic acid comprising the corresponding opposite strand of SEQ ID NO: 1, in the presence of a natural murine diaphanous gene and in a particular embodiment, in the presence of a natural human diaphanous 2 gene). Such primers or probes are at least 12, preferably at least 24, more preferably at least 36 and most preferably at least 96 bases in length. Demonstrating specific hybridization generally requires stringent conditions, i.e. those that (1) employ low ionic strength and high temperature for washing, for example, 0.015 M NaCl/0.0015 M sodium titrate/0.1% SDS at 50° C., or (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C. Another example is use of 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 (g/ml), 0.1% SDS, and 10% dextran sulfate at 42° C., with washes at 42° C. in 0.2×SSC and 0.1% SDS. human diaphanous nucleic acids can also be distinguished using alignment algorithms, such as BLASTX (Altschul et al. (1990) Basic Local Alignment Search Tool, J Mol Biol215, 403–410).

The subject nucleic acids are of synthetic/non-natural sequences and/or are isolated, i.e. unaccompanied by at least some of the material with which it is associated in its natural state, preferably constituting at least about 0.5%, preferably at least about 5% by weight of total nucleic acid present in a given fraction, and usually recombinant, meaning they comprise a non-natural sequence or a natural sequence joined to nucleotide(s) other than that which it is joined to on a natural chromosome. Recombinant nucleic acids comprising the nucleotide sequence of SEQ ID NO: 1, or the subject fragments thereof, contain such sequence or fragment at a terminus, immediately flanked by (i.e. contiguous with) a sequence other than that which it is joined to on a natural chromosome, or flanked by a native flanking region fewer than 10 kb, preferably fewer than 2 kb, which is at a terminus or is immediately flanked by a sequence other than that which it is joined to on a natural chromosome. While the nucleic acids are usually RNA or DNA, it is often advantageous to use nucleic acids comprising other bases or nucleotide analogs to provide modified stability, etc.

The subject nucleic acids find a wide variety of applications including use as translatable transcripts, knock-in/out vectors, hybridization probes, PCR primers, diagnostic nucleic acids, etc.; use in detecting the presence of human diaphanous genes and gene transcripts and in detecting or amplifying nucleic acids encoding additional human diaphanous homologs and structural analogs. Accordingly, the invention provides suitable nucleic acid vectors and tranformed host cells comprising the subject nucleic acids, especially wherein the nucleic acids are operably linked to a homologous or heterologous promoter and expressed in bacterial or insect cells. In diagnosis, human diaphanous hybridization probes find use in identifying wild-type and mutant human diaphanous alleles. Human diaphanous nucleic acids are used to effect and/or modulate cellular expression or intracellular concentration or availability of active human diaphanous.

Methods for effecting the targeted expression of genes encoding the subject modulators are known in the art; see, e.g. Lalwani AK, et al. (1996) Gene Ther Jul;3(7):588–592; Tait, DL et al. (1997) *A Phase I Trial of Retroviral BRCA1sv Gene Therapy in Ovarian Cancer*, Clinical Cancer research, in press and excerpted below; Altenschmidt et al., 1997, J Mol Med 75:259–266; Perales et al. 1997, Proc Natl Acad Sci USA 94:6450–6455; Schmidt et al., 1997, Gene 190:211–216; Oldfield et al., 1993, human Gene Therapy 4: 39–46; Asgari et al., 1997, Int J. Cancer 71:377–382; He D, et al. 1997, Cancer Res 57:1868–1872. In a particular embodiment, the subject human diaphanous polypeptide is introduced by transfecting the cell with a nucleic acid encoding the polypeptide particularly, wherein the nucleic acid comprises SEQ ID NO: 1 or a fragment thereof. Therapeutic nucleic acid compositions may be advantageously combined and/or used in combination with other therapeutic or prophylactic agents, different from the subject compounds. In many instances, administration in conjunction with the subject compositions enhances the efficacy of such agents, see e.g. *Goodman & Gilman's The Pharmacological Basis of Therapeutics*, 9$^{th}$ Ed., 1996, McGraw-Hill.

Without further description, one of ordinary skill in the art can, using the preceding description and the following illustrative examples, make and utilize the compounds of the present invention and practice the claimed methods. The following working examples therefore, specifically point out preferred embodiments of the present invention, and are not to be construed as limiting in any way the remainder of the disclosure. Other generic configurations will be apparent to one skilled in the art. All publications and patent applications cited in this specification are herein incorporated by reference as if each individual publication or patent application were specifically and individually indicated to be incorporated by reference.

EXAMPLES

Example 1

We initially isolated the disclosed natural human diaphanous 1 gene through our studies of hereditary deafness (the actin cytoskeleton of hair cells of the inner ear is critical to hearing). Kindred M of Costa Rica defines the autosomal dominant, fully penetrant, progressive hearing loss DFNA1 (OMIM 124900; 1, 2). Deafness in kindred M is a sensorineural cochleosaccular dysplasia specific to the membranous structures of the inner ear. DFNA1 in kindred M was mapped to a region of 1 cM on chromosome 5q31 by linkage analysis, then a complete 800 kb BAC contig was constructed of the linked region (3). In order to identify all genes in the linked region, we sequenced BACs comprising the contig, after shotgun subcloning each into M13 (4, 5). We developed the computer program SeqHelp to organize sequences from the chromatograms, to call bases and align sequences using the computer programs PHRED and PHRAP, and to apply existing, publicly available software to evaluate the novel genomic sequences (6).

A novel human gene homologous to Drosophila diaphanous (Genbank U11288) and to mouse p140mDia (Genbank U96963, SEQ ID NOS:3, 4) was revealed by genomic sequence of BACs 293C24, and 45M22, 249H5 (7). Given that the mouse and human predicted amino acid sequences were 97% identical for the regions identified from BACs, we estimated the sizes of gaps from the mouse sequence, constructed primers from the human coding sequence, and used these to amplify intervening exons from human cDNA and to carry out 5' RACE on polyA+RNA from lymphoblastoid lines (8). Human diaphanous, or Dia1 (SEQ ID NOS: 1, 2), comprises at least 18 exons with approximately 3800 bp coding sequence and 3=UTR of 918 bp or 1891 bp (9).

In order to screen the Dia1 gene for mutation in the M family, primers were designed to amplify exons and flanking TTAA insertion leads to a frameshift, encoding 21 aberrant amino acids, followed by protein termination that truncates 32 amino acids (Table 1). All 78 affected members of the M kindred are heterozygous for the mutation. The site was wildtype in 330 hearing, control individuals (660 chromosomes) of the following ancestries: 12 Costa Ricans unrelated to the M family, 94 Latin Americans from other countries, 32 Spanish, 154 Europeans (other than Spanish) and North Americans of European ancestry, and 38 African-Americans.

Table 1. DFNA1 mutation in human diaphanous associated with deafness in the Monge family. The wildtype human diaphanous sequence of the splice junctions of the penultimate and ultimate exons and coding sequence of the ultimate exon are shown at top of the figure. Sequence present in the RNA message is capitalized; intronic sequence is in lower case; amino acid sequence is indicated. A guanine residue (g) at the donor splice junction is the site of the DFNA1 mutation. The DFNA1 mutant human diaphanous sequence of the same regions is shown at bottom of the figure. The mutant thymine (T) is indicated in bold. The G→T substitution abrogates the normal donor splice, so splicing occurs instead at the Ag four nucleotides 3' of the normal site. Consequently, TTAA is inserted in the mutant message, causing a frameshift and premature stops, as indicated.

```
Wild Type (see SEQ ID NOS:1, 2)
CCC CGT CAA Ggtaagtaa ... cagaatctctcgtcttctcttgcagCC AAC AGG AAG
Pro Arg Gln                                            Ala Asn Arg Lys GCC GGG TGT GCA GTC ACA TCT CTG CTA GCT TCG GAG CTG ACC AAG GAT
Ala Gly Cys Ala Val Thr Ser Leu Leu Ala Ser Glu Leu Thr Lys Asp GAT GCC ATG GCT GCT GTT CCT GCC AAG GTG TCC AAG AAC AGT GAG ACA
Asp Ala Met Ala Ala Val Pro Ala Lys Val Ser Lys Asn Ser Glu Thr TTC CCC ACA ATC CTT GAG GAA GCC AAG GAG TTG GTT GGC CGT GCA AGC TAA
Phe Pro Thr Ile Leu Glu Glu Ala Lys Glu Leu Val Gly Arg Ala Ser *

Mutant  (see SEQ ID NOS:1, 2)
CCC CGT CAA GTT Aagtaa ... cagaatctctcgtcttctcttgcagC CAA CAG GAA
Pro Arg Gln Val Asn                                    Gln Gln Glu GGC CGG GTG TGC AGT CAC ATC TCT GCT AGC TTC GGA GCT GAC CAA GGA
Gly Arg Val Cys Ser His Ile Ser Ala Ser Phe Gly Ala Asp Gln Gly TGA TGC CAT GGC TGC TGT TCC TGC CAA GGT GTC CAA GAA CAG TGA GAC
 *  Cys His Gly Cys Cys Ser Cys Gln Gly Val Gln Glu Gln  *  Asp ATT CCC CAC AAT CCT TGA GGA AGC CAA GGA GTT GGT TGG CCG TGC AAG CTA A
Ile Pro His Arn Pro  *  Gly Ser Gln Gly Val Gly Trp Pro Cys Lys Lue
``` splice junctions from genomic DNA of affected and unaffected members of the M family and from controls. Each product was screened for single strand conformation polymorphisms (SSCP). Variant bands were gel-purified, reamplified, and sequenced (10).

A guanine to thymine substitution in the splice donor of the penultimate exon of human Dia1 was observed in affected members of the M kindred. The guanine to thymine substitution at this site disrupts the canonical splice donor sequence AAGgtaagt. In order to determine the consequences of this mutation at the level of RNA message, polyA+cDNA was prepared from lymphoblast cell lines of three affected members of the M kindred and from unaffected family members and unrelated, unaffected controls. Insertion of TTAA was observed in cDNA of affected individuals. The mechanism for the insertion was splicing at a cryptic site four basepairs 3' of the wildtype site. The Expression of human Dia1 message in brain, heart, placenta, lung, kidney, pancreas, liver and skeletal muscle was confirmed by Northern hybridization. A single transcript of 4.7 kb was observed in all tissues with highest expression in skeletal muscle. RNA from lymphoblastoid cell fines of affected and unaffected members of the M family similarly revealed a single transcript of 4.7 kb in all individuals, consistent with a 4 bp insertion in the mutant message. Expression of the human Dia1 gene in the cochlea was confirmed by RT-PCR of cochlear RNA using PCR primers that amplified the region of Dia1 that harbors the mutation in family M (10, 11). The sequence of the RT-PCR product from cochlear RNA was wild type. Hence, if alternate splice forms of Dia1 exist, normal cochlear transcripts include the region of Dia1 that is improperly spliced in affected members of kindred M.

Human Dia1, mouse p140mDia, and Drosophila diaphanous proteins are homologs of Saccharomyces cervisiae gene Bnilp (12). The genes encoding these proteins are members of the formin gene family, which also includes the mouse limb deformity gene, Drosophila cappuccino, Aspergillus nidulins gene sepA, and *S.pombe* genes fus1 and cdc12 (13). These genes are involved in cytokinesis and establishment of cell polarity. All formins share Rho-binding domains formin-homology domains in the C-terminal region (12). Multiple mutants of mouse formin have been characterized (13). A truncated mouse formin allele Id$^{ln2}$ lacking the 42 C-terminal amino acids leads to mislocalization of the formin protein to the cytoplasm (14).

We find that Dia1 affects hearing through the regulation of actin polymerization in hair cells. Actin polymerization involves proteins known to interact with diaphanous in Drosophila and mouse. The protein profilin binds actin monomers and is a regulator of actin polymerization (15). Mammalian and Drosophila diaphanous are effectors of Rho (12). Diaphanous acts in a Rho-dependent manner to recruit profilin to the membrane, where it promotes actin polymerization. As predicted by this model, transient expression of p140mDia induced homogeneous actin filament formation in COS cells (7). Rho-induced actin polymerization is conserved from yeast to mammals.

The DFNA1 mutation observed in Dia1 in the M family is relatively subtle, in that it affects only the C-terminal 52 amino acids. Given that human Dia1 appears to be ubiquitously expressed, and the only observed phenotype in the M family is hearing loss, we conclude that the hair cells of the cochlea are particularly sensitive to proper maintenance of the actin cytoskeleton and that this mutation can effect a partial loss of function of the Dia1 protein. One process in the inner ear uniquely sensitive to disruption of actin polymerization is amplification of sound reception by the inner hair cells, which is due to the concerted action of outer hair cells and pillar cells. Relay of kinetic energy from outer hair cells to inner hair cells relies critically on the presence of a rigid structure of actin fibers. Additional structural support in hair cells is provided by the cuticular plate, a dense network of actin fibers at the apical ends of hair cells into which stereocilia are anchored. The DFNA1 mutation of Dia1 can impair maintenance of the dynamic organization of the actin fibers of the cuticular plate.

Hair cell stereocilia provides an additional site that can be affected by the aberrant protein. The structural support providing rigidity to the stereocilia is comprised largely of cross-linked actin filaments packed in a paracrystaline array (16). Upon acoustic overstimulation, the paracrystal is disordered (17) and Dia1 is involved in the reordering of the array. In the M family, mutant Dia1 can compete with the wild-type protein to repair damage from normal exposure to sound. Trangenic mice with the DFNA1 mutation in p140mDia are used to characterize the effects of acoustic exposures.

A second human homolog of Drosophila diaphanous (SEQ ID NOS:5, 6) was revealed during the cloning of Dia1. This second human diaphanous, Dia2, maps to chromosome Xq22 (18). Non-syndromic X-linked deafness, DFN2, also maps to Xq22 (19), indicating the Dia2 gene as a candidate gene for DFN2 hearing loss. In fact, we disclose that mutations in Dia1 and/or Dia2 can affect a wide range of pathologies in humans, including deafness, infertility, neuropathology, etc. Furthermore, Dia1 and/or Dia2 mutations can also manifest symptoms characterized as Perrault syndrome, Pallister P D, Opitz J M, Am J Med Genet 1979;4(3):239–246; Gottschalk M E, Coker S B, Fox L A, Am J Med Genet 1996 Nov 11;65(4):274–276. Accordingly, the disclosed modulators, nucleic acids and binding agents find a wide variety of diagnostic, biotechnological and clinical applications.

REFERENCES

1. Leon PE, et al., Amer J Hum Genet 33:209–214 (1981); Leon PE, Raventos H, Lynch E, Morrow J, King MC Proc Natl Acad Sci USA 89:181–184 (1992)
2. This project has been approved by the Committee on Human Subjects in Research of the Ministry of Health of Costa Rica, and by the Human Subjects Division of the Institutional Review Board of the University of Washington. The criterion for deafness in the family is a hearing threshold greater than 50 dB at 250 Hz and 500 Hz. Of the participants, 78 are deaf and 69 are older than 30 years with normal hearing. All deaf relatives are included in the analysis, as are all hearing relatives older than age 30 years and all persons marrying into the family. No relatives younger than age 30 with normal hearing are included in the analysis Cell lines were established from lymphocytes of 147 informative relatives using established techniques (1).
3. Lynch ED, Lee M K, Lalwani A, Jackler R K, Sweetow R W, Raventos H, Kujawa S, Morrow J, King M C, Leon PE Localization, physical mapping, and description of the clinical phenotype of DFNA1, a gene for post-lingual non-syndromic deafness on chromosome 5q31. In review.
4. Kim U J, et al., Genomics 34:213–218 (1996)
5. Sequencing of BACs was performed as follows: 30 ug of BAC DNA was sonicated to 50 to 5000 bp, then treated with mung bean exonuclease. Blunt ended fragments were electrophoresed on agarose gels, DNA in the 1.5 kb to 3 kb range was excised from the gel for DNA isolation with a Qiaex gel extraction kit. Recovered fragments were ligated into SmaI digested, phosphatase-treated, M13mpl8 vector. Ligations were electroporated into *E. coli* strain DH12S. Transformations were plated in LB top agarose with DH12S lawn cells, X-gal, and IPTG, onto LB plates and incubated overnight at 37 C. The following day, clear plaques were picked and inoculated into 1 mL of LB with DH12S host cells in 96 well 2mL plates. Phage cultures were incubated for 24 hours at 37 C, shaking at 250 rpm. Single stranded M13 DNA was prepared by standard methods using PEG precipitation of phage particles and NaI solution to remove proteins. A detailed copy of the DNA preparation method can be found on the Internet at <hyper text transfer protocol:// chroma.mbt.washington.edu/~kwseq/preps/amy_NaI_prep.html> This preparation method yielded 1–2 ug of M13 DNA for sequencing. The resulting DNA pellets were diluted in 30 ul of water, and 6 microliters used in 10 microliter sequencing reactions with dichloroRhodamine Dye Terminator Chemistry from ABI. The remaining DNA was stored at −80 C for future use. Sequencing reactions were precipitated with 100 microliters of 70% EtOH and 5mM MgCl2 at room temperature for 15 minutes. Precipitated reactions were pelleted by centrifugation for 15 minutes at 3500 rpm in Beckman SH-3000 rotor with 96 well plate adapters. Supernatants were removed by centrifugation of the inverted plate at 500 rpm for 1 minute then pellets dried at 37 C for 5 minutes. Pellets were resuspended in 3 microliters of formamide loading dye, denatured at 95 C for two minutes, then placed on ice. One microliter of sequencing reaction was loaded onto a 36 cM Longranger gel (FMC) and electrophoresed on an ABI377 automated sequencer. ABI377 collection software Version 1.1 was used to support 48-well combs and nine hour data collection in the 2× collection mode. The chromatograms generated by ABI Sequence Analysis software version 3.0 were transferred to a UNIX-based Sun workstation for contig assembly and blast analysis. The computer program PHRED (Green P and Ewing B. 1996. hyper text transfer protocol://world wide web.bozeman.mbt.washington.edu/ phrap.docs/ phred.html) was used to assign bases to the electropherograms. After eliminating vector sequences, the program PHRAP (Green P and Ewing B. 1996. hyper text transfer protocol://world wide web.bozeman.mbt.washington.edu/ phrap.docs/ phrap.html) was used to analyze the sequences, identify overlapping individual sequences, and assemble them into contigs. To achieve approximately 6 fold coverage of a region, we sequenced an average of 600 M13 subclones per BAC.

6. The SeqHelp program incorporates several sequence analysis programs and creates output in HTML files for browsing with any WWW browser (Lee et al Genomics submitted). The core programs used by Seqhelp are PHRED to read the ABI sequence files and assign bases, PHRAP to generate contigs of overlapping sequences, Repeat Masker (Arian Smit) to identify and mask common repetative elements prior to database searching, and BLAST (Altschul S, Gish W, Miller W, Myers E, Lipman D J Mol Biol 215:403–410 (1990)) comparison of project specific sequences to the NR and dbEST databases at the NCBI. An example of the SeqHelp output for analysis of the BRCA1 genomic region is available online at <hyper text transfer protocol://polaris.mbt.washington.edu>

7. Castrillon D H, Wasserman S A. Development 120:3367–3377 (1994); Watanabe N, et al., EMBO J 16:3044–3056 (1997)

8. Polyadenylated RNA [poly(A+)] RNA was purified from lymphoblastoid cell lines using oligo-dT cellulose (Sambrook J, Fritsch E F, Maniatis T Molecular Cloning. Cold Srping Harbor (1989)). 5' cDNA sequence was obtained using the 5' RACE (Rapid Amplification of cDNA Ends) System, Version 2.0 (Gibco BRL). 5' RACE was performed on 1 microgram of polyA+lymphoblast RNA according to the manufacturer's specifications. First strand cDNA synthesis was primed using the human diaphanous specific primer H2a (5'-AGTCATCCATCTCCATGCGAATG-3') (SEQ ID NO:7). Following cDNA synthesis and homopolymeric 3' tailing with Tdt (terminal deoxynucleotidyl transferase), first strand cDNA was amplified using the human diaphanous specific primer H2b (5'-ATGCGAATGTCATCCAGCCGTC-3') (SEQ ID NO:8), a nested primer which anneals 3' to H2a. 5' RACE products of approximately 1 kb were gel purified and TA cloned into the pGEM-T vector (Invitrogen) according to the manufactures directions. 5' RACE clones were amplified using M13-40F and M13-40R PCR products of 5' RACE clones were purified. Templates were sequenced using M13-40 R primers and the gene specific primers H6f (5'-TTGCGGGATATGCCTCTG-3') (SEQ ID NO:9) and H7a (5'-GGTTGTTGTTGAGAGACACAC-3') (SEQ ID NO: 10). Sequencing was done using dichloroRhodamine Dye Terminators (ABI) and an ABI 377 sequencer.

9. IMAGE clones 51234, 52194, 124697, 261240, 262633, 612749, and 926002 are cDNA clones of portions of human diaphanous (Lennon G, Auffray C, Polymeropoulos M, Soares MB. Genomics.33:151–152 (1996)). The ESTs for all clones are confined to the most 3' exon of human diaphanous.

10. PCR primers used to amplify the the variant sequence which includes the involved splice donor region are Dia9F (5'-TGTGGGAGAGGGGAAATCAAG-3') (SEQ ID NO:11) and Dia9R (5'-TTGCTCTTTAGCCGCAGACTGG-3') (SEQ ID NO: 12). The 278bp product was labeled by incorporation of a-p32 dCT? during PCR, diluted 1:10 in formamide loading buffer, denatured at 95 C for 2 minuted, then placed on ice for 10 minutes. Eight microliters of each sample was loaded onto an MDE (FMC Biochem) gel and electrophoresed at 6W for 18 hours at room temperature to resolve single strand comformation polymorphisms. Gels were dried and exposed to X-ray film for 18 hours. Variant bands on SSCP gels were individually excised from dried gels, eluted with water, and used as a template for reamplification with the Dia9F and Dia9R primers. PCR products were purified by centrifugation through 300 microliters of Sephacryl-300 resin then sequenced using the Dia 9F and Di9R primers. Sequencing was done using dichloroRhodamine Dye Terminators (ABI) and an ABI 377 sequencer as described in footnote 2. PCR amplification for cDNA analysis of the variant region was done using primers Dia8–10F (5'-CGGCGGAAGACAGAAGAAAAG-3') (SEQ ID NO: 13) and Dia8–10R (5'-TAGCAGAGATGTGACTGCACACCC-3') (SEQ ID NO: 14) which are designed to amplify a 234 bp product that spans the second to last exon and ends in the last exon of human mDia. PCR products were labeled and analyzed by SSCP as describe above. Variant bands were sequenced using the Dia8–10F and Dia8–10R primers.

11. Total cochlear RNA was extracted using the guanidine isothiocyanate method (Chirgwin J M, Przybyla A E, MacDonald R J, Rutter W J. Biochemistry 18:5294–5299 (1979). One microgram of total cochlear RNA was used in a 50 microliter random primed reverse transcription reaction with Superscript MMLV RTase (Gibco/BRL) according to manufacturers instructions. Five microliters of the resulting cDNA was used as template in a 50 microliter gene specific PCR reaction using the Dia8–10F and Dia8–10R primers (10). PCR products were resolved on a 2% agarose gel and visualized with ethidium bromide staining.

12. Evangelista M, et al., Science 276:118–121 (1997); Narumiya S, Ishizaki T, Watanabe N FEBS Lett 410:68–72 (1997)

13. Woychik R P, et al., Nature 346:850–853 (1990); Maas R L, et al., Nature 346:853–855 (1990); Maas R L, et al., Am J Hum Genet 48:687–695 (1991); Vogt T F, et al., Proc Natl Acad Sci USA 90:5554–5558 (1993); Wang C C, et al., Genomics 39:303–311 (1997); Wynshaw-Boris A, et al., Mol Med 3:372–384 (1997); Frazier J A, et al., Curr Biol 7:414–417 (1997)

14. Chan D C, Leder P J Biol Chem 271:23472–23477 (1996)

15. Theriot J A, Mitchison T J. Cell 75:835–838 (1993).

16. Flock A, et al., J Cell Biol 75:339–343 (1977); Itoh M Hearing Res 6:227–289 (1982)

17. Tilney L G, Saunders J C, Egelman E H, DeRosier D J Hear Res 7:181–197 (1982)

18. Dia2 is represented by several IMAGE clones including 626664, a 3.1 kb cDNA clone from a HeLa cDNA library. When searched against the Genbank database, a portion of this clone was identical to genomic DNA from PAC 117P19, sequenced and mapped by the Sanger Center to Xq21.3. The Drosophila Related Expressed Sequences homepage <hyper text transfer protocol://world wide web.tigem.it/LOCAL/drosophila/dros.html>(Banfi S, Borsani G, Bulfome A, Ballbio A. Hum Mol Genet 6:1745–1753 (1997)) indicates that a human homolog of Drosophila diaphanous maps to human chromosome Xq22.

19. Tyson J, et al., Hum Mol Genet 5:2055–2060 (1996)

Example 2
Retroviral hDia1sv Gene Therapy

LXSN-hDia1 vector is constructed by cloning a hDia1 cDNA into the well-characterized retroviral vector LXSN (Holt J T, et al. Nature Genetics 12:298–302,1996). Retroviral vector is manufactured under cGMP (current Good Manufacturing Practices) conditions employing a CellCube (Corning-Costar, Cambridge, Mass.) apparatus perfused with Aim V media (Life Technologies, Gaithersburg, Md.) under continuous monitoring of pH and $O_2$. Once the oxygen and glucose consumption are consistent and appropriate, supernatant is collected as long as the oxygen and glucose levels assure optimal vector production. No post-production manufacturing is performed on the supernatants collected in Aim V media which are frozen and stored in aliquots at –70° C. The titer of the vector preparations is determined by counting the number of particles present that confer G418 resistance to transduced MCF-7 cells, employing appropriate dilutions. Vector from this production lot is confirmed negative for bacterial, mycoplasm, viral contamination and endotoxin. Replication-competent retroviruses are confirmed absent using PG4 indicator cells following amplification on Mus Dunni. In addition to the tests performed on the clinical grade vector described above, a number of tests are performed on the producer cells in the master cell bank: including tests for pathogenic viruses and replication-competent retroviruses. A toxicity study is done in mice: 92 Balb/C female mice were injected with either high-dose gene therapy (clinical grade) or low-dose (clinical grade diluted 1:10 in AimV) once daily for four days with and without oyster glycogen pre-treatment (48hrs prior) to simulate patient peritonitis. Mice are harvested at 4 hours, 24 hours, 48 hours, one week and two weeks post-injections, at which time blood and 14 tissues are removed for histological and molecular assays.

Vector Administration.

Aliquots of vector are thawed and 8 ug/ml of polybrene is added sterilely. Infusions of vector into patients are initiated within one hour of thawing the vector aliquot. The initial dose (between 3 mls to 300 mls depending on the dose escalation) is given with 1.5 liters of sterile saline ip and the three subsequent doses are given with sterile saline to a total volume of 100–300 ml.

Study design.

Patients undergo initial placement of a peritoneal port-a-cath for access to the peritoneal cavity and are subsequently treated for four consecutive days with intraperitoneal LXSN-hDia1 gene therapy. The starting dose level in patients is that dose which corresponds to the no effect dose in mice ($10^8$), and a half-log dose escalation is performed up to the dose which corresponds to the LD10 dose in mice ($10^{10}$). Five dose levels are studied: $10^8$, $3.3 \times 10^8$, $10^9$, $3.3 \times 10^9$, and $10^{10}$ viral particles. Objective endpoints to assess toxicity include: daily blood and peritoneal sample to evaluate peritoneal fluid cell counts, hematological cell counts, serum chemistries, bacterial cultures as needed, vector stability, viral uptake by cells, expression of hDia1 gene and presence of antibodies to vector envelope proteins. At four week intervals patients are evaluated for response to therapy; and if positive, retreatment allowed. The first three patients are treated at the first dose level. After the next higher dose level is tolerated by a new patient, any repeat patients are graduated to that dose. The dose is again elevated after three patients tolerate it without toxicity.

Detection of vector stability and expression.

DNA is prepared from cell samples by hypotonic lysis, digestion with proteinase K (Boehringer Mannheim, Indianapolis, Ind.) and SDS, followed by phenol/chloroform extraction and ethanol precipitation. DNA is prepared from tissue samples by freezing samples at –70° C. and then finely mincing cold samples with a blade, prior to treatment with proteinase K as described above. RNA are purified from cells by lysis in guanidinium isothiocyanate.

PCR primers specific for the neo sequences within the LXSN-hDia1sv vector are employed for determination of vector presence and stability within patient samples. RT-PCR is performed by our published methods (Thompson, M. E., et al. Nature Genetics 9, 444–450,1995.).

Southern blotting of Ava I digested DNA is performed with a human hDia1 probe. Percent transduction is estimated by quantitating hybridization with the phosphoimager and then comparing hybridization of the presumed haploid vector lower band to that of the diploid hDia1 upper band (percent transduction=2X vector signal/genomic signal× 100). Nuclease protection assays are performed with MRNA isolated from patient samples and then probed with a T7 polymerase generated probe from a digested hDia1 DNA template. Radiolabelled probe is hybridized with patient MRNA samples for 8 hours at 52° C. in 80% formamide and then digested for 30 minutes with RNAse A and RNAse T1 at 25° C. and then products resolved on a 10% denaturing polyacrylamide gel (supra).

Immunologic studies

Patient plasmas and peritoneal fluids are frozen and then used for measurements of CH50 or western blotting for envelope antibodies. CH50 is performed following manufacturer's instructions on plasma and peritoneal samples, using antibody-sensitized sheep erythrocytes (Sigma, St. Louis, Mo.). Basically, patient peritoneal fluid or sera are incubated with antibody-sensitized sheep erythrocytes in sodium barbital buffer for 30 minutes at 37° C. The extent of antibody-dependent lysis is then determined by pelleting unlysed red cells and measuring hemolysis in the supernatant by spectrophotometry against a standard curve. Standard complement serum (Sigma, St. Louis, Mo.) are employed as a control standard.

What is claimed is:

1. An isolated polypeptide having an amino acid sequence comprising, SEQ ID NO:2 or fragments thereof wherein said polypeptide modulates actin polymerization or specifically binds human Rho or profilin polypeptides.

2. An isolated polypeptide according to claim 1, wherein the amino acid sequence comprising at least 100 contiguous residues of SEQ ID NO:2.

3. A polypeptide according to claim 1, wherein the amino acid sequence comprises SEQ ID NO:2, residues 121–151.

4. A polypeptide according to claim 1, wherein the amino acid sequence comprises SEQ ID NO:2, residues 197–205.

5. A polypeptide according to claim 1, wherein the amino acid sequence comprises SEQ ID NO:2, residues 350–382.

6. A polypeptide according to claim 1, wherein the amino acid sequence comprises SEQ ID NO:2, residues 439–454.

7. A polypeptide according to claim 1, wherein the amino acid sequence comprises SEQ ID NO:2, residues 515–524.

8. A polypeptide according to claim 1, wherein the amino acid sequence comprises SEQ ID NO:2, residues 551–569.

9. A polypeptide according to claim 1, wherein the amino acid sequence comprises SEQ ID NO:2, residues 590–610.

10. A polypeptide according to claim 1, wherein the amino acid sequence comprises SEQ ID NO:2, residues 611–630.

11. A polypeptide according to claim 1, wherein the amino acid sequence comprises SEQ ID NO:2, residues 631–650.

12. A polypeptide according to claim 1, wherein the amino acid sequence comprises SEQ ID NO:2, residues 651–670.

13. A polypeptide according to claim 1, herein the amino acid sequence comprises SEQ ID NO:2, residues 761–780.

14. A polypeptide according to claim 1, wherein the amino acid sequence comprises SEQ ID NO:2, residues 888–900.

15. A polypeptide according to claim 1, wherein the amino acid sequence comprises SEQ ID NO:2, residues 1041–1050.

16. A polypeptide according to claim 1, wherein the amino acid sequence comprises SEQ ID NO:2, residues 1195–1208.

17. A method of screening for an agent which modulates the binding of a human diaphanous polypeptide to a binding target, said method comprising the steps of:

contacting a polypeptide according to claim 1 with a binding target of said polypeptide in the presence of a candidate agent, and detecting or measuring the binding of the polypeptide to said binding target, wherein a difference in the amount of said binding relative to the amount of binding in the absence of the candidate agent indicates that the agent modulates the binding of said polypeptide to said binding target, wherein said binding target is a human Rho or profilin polypeptide.

18. A method for modulating the interaction of a natural human diaphanous protein with a natural human diaphanous binding target comprising the step of contacting said protein or said binding target with a polypeptide according to claim 1, whereby said polypeptide modulates the binding of said protein to said binding target.

19. A method of making an antibody which specifically binds a human diaphanous polypeptide, said method comprising the steps of:

immunizing a nonhuman host with a polypeptide according to claim 1 to elicit a human diaphanous polypeptide specific antibody in said host.

* * * * *

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
      (A) LENGTH: 3747 base pairs
      (B) TYPE: nucleic acid
      (C) STRANDEDNESS: single -continued

```
        (D) TOPOLOGY: linear (ii) MOLECULE TYPE: other nucleic acid (ix) FEATURE:
         (A) NAME/KEY: CDS
         (B) LOCATION: 1..3744

(xi) SEQUENCE DESCRIPTION: SEQ ID NO:1:

ATG GAG CCG CCC GGC GGG AGC CTG GGG CCC GGC CGC GAG ACC CGG GAC     48
Met Glu Pro Pro Gly Gly Ser Leu Gly Pro Gly Arg Glu Thr Arg Asp
 1               5                  10                  15

AAG AAG AAG GGC CGG AGC CCA GAT GAG CTG CCC TCG GCG GGC GGC GAC     96
Lys Lys Lys Gly Arg Ser Pro Asp Glu Leu Pro Ser Ala Gly Gly Asp
            20                  25                  30

GGC GGC AAA TCT AAG AAA TTT CTG GAG AGA TTT ACC AGC ATG AGA ATT    144
Gly Gly Lys Ser Lys Lys Phe Leu Glu Arg Phe Thr Ser Met Arg Ile
        35                  40                  45

AAG AAG GAG AAG GAA AAG CCC AAT TCT GCT CAT AGA AAT TCT TCT GCA    192
Lys Lys Glu Lys Glu Lys Pro Asn Ser Ala His Arg Asn Ser Ser Ala
 50                  55                  60

TCA TAT GGG GAT GAT CCC ACA GCA CAG TCA TTG CAA GAT GTT TCA GAT    240
Ser Tyr Gly Asp Asp Pro Thr Ala Gln Ser Leu Gln Asp Val Ser Asp
 65                  70                  75                  80

GAA CAA GTG CTG GTT CTC TTT GAA CAG ATG CTG CTG GAT ATG AAC CTG    288
Glu Gln Val Leu Val Leu Phe Glu Gln Met Leu Leu Asp Met Asn Leu
                 85                  90                  95

AAT GAG GAG AAA CAG CAA CCT TTG AGG GAG AAG GAC ATC ATC ATC AAG    336
Asn Glu Glu Lys Gln Gln Pro Leu Arg Glu Lys Asp Ile Ile Ile Lys
            100                 105                 110

AGG GAG ATG GTG TCC CAA TAC TTG TAC ACC TCC AAG GCT GGC ATG AGC    384
Arg Glu Met Val Ser Gln Tyr Leu Tyr Thr Ser Lys Ala Gly Met Ser
        115                 120                 125

CAG AAG GAG AGC TCT AAG TCT GCC ATG ATG TAT ATT CAG GAG TTG AGG    432
Gln Lys Glu Ser Ser Lys Ser Ala Met Met Tyr Ile Gln Glu Leu Arg
130                 135                 140

TCA GGC TTG CGG GAT ATG CCT CTG CTC AGC TGC CTG GAG TCC CTT CGT    480
Ser Gly Leu Arg Asp Met Pro Leu Leu Ser Cys Leu Glu Ser Leu Arg
145                 150                 155                 160

GTG TCT CTC AAC AAC AAC CCT GTC AGT TGG GTG CAA ACA TTT GGT GCT    528
Val Ser Leu Asn Asn Asn Pro Val Ser Trp Val Gln Thr Phe Gly Ala
                165                 170                 175

GAA GGC TTG GCC TCC TTA TTG GAC ATT CTT AAA CGA CTT CAT GAT GAG    576
Glu Gly Leu Ala Ser Leu Leu Asp Ile Leu Lys Arg Leu His Asp Glu
            180                 185                 190

AAA GAA GAG ACT GCT GGG AGT TAC GAT AGC CGG AAC AAG CAT GAG ATC    624
Lys Glu Glu Thr Ala Gly Ser Tyr Asp Ser Arg Asn Lys His Glu Ile
        195                 200                 205

ATT CGC TGC TTG AAA GCT TTT ATG AAC AAC AAG TTT GGA ATC AAG ACC    672
Ile Arg Cys Leu Lys Ala Phe Met Asn Asn Lys Phe Gly Ile Lys Thr
210                 215                 220

ATG TTG GAG ACA GAA GAA GGA ATC CTA CTG CTG GTC AGA GCC ATG GAT    720
Met Leu Glu Thr Glu Glu Gly Ile Leu Leu Leu Val Arg Ala Met Asp
225                 230                 235                 240

CCT GCT GTT CCC AAC ATG ATG ATT GAT GCA GCT AAG CTG CTT TCT GCT    768
Pro Ala Val Pro Asn Met Met Ile Asp Ala Ala Lys Leu Leu Ser Ala
                245                 250                 255

CTT TGT ATT CTA CCG CAG CCA GAG GAC ATG AAT GAA AGG GTT TTG GAG    816
Leu Cys Ile Leu Pro Gln Pro Glu Asp Met Asn Glu Arg Val Leu Glu
            260                 265                 270

GCA ATG ACA GAA AGA GCT GAG ATG GAT GAA GTG GAA CGT TTC CAG CCG    864
```

```
                                                                    -continued Ala Met Thr Glu Arg Ala Glu Met Asp Glu Val Glu Arg Phe Gln Pro
        275                 280                 285

CTG CTG GAT GGA TTA AAA AGT GGA ACC ACT ATT GCA CTG AAG GTT GGA     912
Leu Leu Asp Gly Leu Lys Ser Gly Thr Thr Ile Ala Leu Lys Val Gly
        290                 295                 300

TGC CTA CAG CTG ATC AAT GCT CTC ATC ACA CCA GCG GAG GAA CTT GAC     960
Cys Leu Gln Leu Ile Asn Ala Leu Ile Thr Pro Ala Glu Glu Leu Asp
305                 310                 315                 320

TTC CGA GTT CAC ATC AGA AGT GAA CTG ATG CGT TTG GGG CTA CAT CAG    1008
Phe Arg Val His Ile Arg Ser Glu Leu Met Arg Leu Gly Leu His Gln
                325                 330                 335

GTG TTG CAG GAC CTT CGA GAG ATT GAA AAT GAA GAT ATG AGA GTG CAA    1056
Val Leu Gln Asp Leu Arg Glu Ile Glu Asn Glu Asp Met Arg Val Gln
        340                 345                 350

CTA AAT GTG TTT GAT GAA CAA GGG GAA GAG GAT TCC TAT GAC CTG AAG    1104
Leu Asn Val Phe Asp Glu Gln Gly Glu Glu Asp Ser Tyr Asp Leu Lys
        355                 360                 365

GGA CGG CTG GAT GAC ATT CGC ATG GAG ATG GAT GAC TTT AAT GAA GTC    1152
Gly Arg Leu Asp Asp Ile Arg Met Glu Met Asp Asp Phe Asn Glu Val
        370                 375                 380

TTT CAG ATT CTC TTA AAC ACA GTG AAG GAT TCA AAG GCA GAG CCA CAC    1200
Phe Gln Ile Leu Leu Asn Thr Val Lys Asp Ser Lys Ala Glu Pro His
385                 390                 395                 400

TTC CTT TCC ATC CTG CAG CAC TTA CTC TTG GTC CGA AAT GAC TAT GAG    1248
Phe Leu Ser Ile Leu Gln His Leu Leu Leu Val Arg Asn Asp Tyr Glu
                405                 410                 415

GCC AGA CCT CAG TAC TAT AAG TTG ATT GAA GAA TGT ATT TCC CAG ATA    1296
Ala Arg Pro Gln Tyr Tyr Lys Leu Ile Glu Glu Cys Ile Ser Gln Ile
            420                 425                 430

GTT CTG CAC AAG AAC GGG GCT GAT CCT GAC TTC AAG TGC CGG CAC CTC    1344
Val Leu His Lys Asn Gly Ala Asp Pro Asp Phe Lys Cys Arg His Leu
        435                 440                 445

CAG ATT GAG ATT GAG GGA TTA ATT GAT CAA ATG ATT GAT AAG ACA AAG    1392
Gln Ile Glu Ile Glu Gly Leu Ile Asp Gln Met Ile Asp Lys Thr Lys
        450                 455                 460

GTG GAG AAA TCT GAA GCC AAA GCT GCA GAG CTG GAA AAG AAG TTG GAC    1440
Val Glu Lys Ser Glu Ala Lys Ala Ala Glu Leu Glu Lys Lys Leu Asp
465                 470                 475                 480

TCA GAG TTA ACA GCC CGA CAT GAG CTA CAG GTG GAA ATG AAA AAG ATG    1488
Ser Glu Leu Thr Ala Arg His Glu Leu Gln Val Glu Met Lys Lys Met
                485                 490                 495

GAA AGT GAC TTT GAG CAG AAG CTT CAA GAT CTT CAG GGA GAA AAA GAT    1536
Glu Ser Asp Phe Glu Gln Lys Leu Gln Asp Leu Gln Gly Glu Lys Asp
            500                 505                 510

GCA CTG CAT TCT GAA AAG CAG CAA ATT GCC ACA GAG AAA CAG GAC CTG    1584
Ala Leu His Ser Glu Lys Gln Gln Ile Ala Thr Glu Lys Gln Asp Leu
        515                 520                 525

GAA GCA GAG GTG TCC CAG CTC ACA GGA GAG GTT GCC AAG CTG ACA AAG    1632
Glu Ala Glu Val Ser Gln Leu Thr Gly Glu Val Ala Lys Leu Thr Lys
        530                 535                 540

GAA CTG GAA GAT GCC AAG AAA GAA ATG GCT TCC CTC TCT GCG GCA GCT    1680
Glu Leu Glu Asp Ala Lys Lys Glu Met Ala Ser Leu Ser Ala Ala Ala
545                 550                 555                 560

ATT ACT GTA CCT CCT TCT GTT CCT AGT CGT GCT CCT GTT CCC CCT GCC    1728
Ile Thr Val Pro Pro Ser Val Pro Ser Arg Ala Pro Val Pro Pro Ala
                565                 570                 575

CCT CCT TTA CCT GGT GAC TCT GGC ACT ATT ATT CCA CCA CCT GCT        1776
Pro Pro Leu Pro Gly Asp Ser Gly Thr Ile Ile Pro Pro Pro Ala
            580                 585                 590
```

```
                                                     -continued

CCT GGG GAT AGT ACC ACT CCT CCT CCT CCT CCA CCA CCA CCA CCT CCA     1824
Pro Gly Asp Ser Thr Thr Pro Pro Pro Pro Pro Pro Pro Pro Pro Pro
            595                 600                 605

CCA CCT CCT TTA CCT GGA GGT ACT GCT ATC TCT CCA CCC CCT CCT TTG     1872
Pro Pro Pro Leu Pro Gly Gly Thr Ala Ile Ser Pro Pro Pro Pro Leu
610                 615                 620

TCT GGG GAT GCT ACC ATC CCT CCA CCC CCT CCT TTG CCT GAG GGT GTT     1920
Ser Gly Asp Ala Thr Ile Pro Pro Pro Pro Pro Leu Pro Glu Gly Val
625                 630                 635                 640

GGC ATC CCT TCA CCC TCT TCT TTG CCT GGA GGT ACT GCC ATC CCC CCA     1968
Gly Ile Pro Ser Pro Ser Ser Leu Pro Gly Gly Thr Ala Ile Pro Pro
                645                 650                 655

CCT CCT CCT TTG CCT GGG AGT GCT AGA ATC CCC CCA CCA CCT CCT         2016
Pro Pro Pro Leu Pro Gly Ser Ala Arg Ile Pro Pro Pro Pro Pro
            660                 665                 670

TTG CCT GGG AGT GCT GGA ATT CCC CCC CCA CCT CCT CCC TTG CCT GGA     2064
Leu Pro Gly Ser Ala Gly Ile Pro Pro Pro Pro Pro Leu Pro Gly
            675                 680                 685

GAA GCA GGA ATG CCA CCT CCT CCT CCC CCT CTT CCT GGT GGT CCT GGA     2112
Glu Ala Gly Met Pro Pro Pro Pro Pro Pro Leu Pro Gly Gly Pro Gly
690                 695                 700

ATC CCT CCA CCT CCT CCA TTT CCC GGA GGC CCT GGC ATT CCT CCA CCT     2160
Ile Pro Pro Pro Pro Pro Phe Pro Gly Gly Pro Gly Ile Pro Pro Pro
705                 710                 715                 720

CCA CCC GGA ATG GGT ATG CCT CCA CCT CCC CCA TTT GGA TTT GGA GTT     2208
Pro Pro Gly Met Gly Met Pro Pro Pro Pro Phe Gly Phe Gly Val
                725                 730                 735

CCT GCA GCC CCA GTT CTG CCA TTT GGA TTA ACC CCC AAA AAG CTT TAT     2256
Pro Ala Ala Pro Val Leu Pro Phe Gly Leu Thr Pro Lys Lys Leu Tyr
            740                 745                 750

AAG CCA GAG GTG CAG CTC CGG AGG CCA AAC TGG TCC AAG CTT GTG GCT     2304
Lys Pro Glu Val Gln Leu Arg Arg Pro Asn Trp Ser Lys Leu Val Ala
            755                 760                 765

GAG GAC CTC TCC CAG GAC TGC TTC TGG ACA AAG GTG AAG GAG GAC CGC     2352
Glu Asp Leu Ser Gln Asp Cys Phe Trp Thr Lys Val Lys Glu Asp Arg
770                 775                 780

TTT GAG AAC AAT GAA CTT TTC GCC AAA CTT ACC CTT ACC TTC TCT GCC     2400
Phe Glu Asn Asn Glu Leu Phe Ala Lys Leu Thr Leu Thr Phe Ser Ala
785                 790                 795                 800

CAG ACC AAG ACC AAG AAG GAT CAA GAA GGT GGA GAA GAA AAG AAA TCT     2448
Gln Thr Lys Thr Lys Lys Asp Gln Glu Gly Gly Glu Glu Lys Lys Ser
                805                 810                 815

GTG CAA AAG AAA AAA GTA AAA GAG TTA AAG GTG TTG GAT TCA AAG ACA     2496
Val Gln Lys Lys Lys Val Lys Glu Leu Lys Val Leu Asp Ser Lys Thr
            820                 825                 830

GCC CAG AAT CTC TCA ATC TTT TTG GGT TCC TTC CGC ATG CCC TAT CAA     2544
Ala Gln Asn Leu Ser Ile Phe Leu Gly Ser Phe Arg Met Pro Tyr Gln
            835                 840                 845

GAG ATT AAG AAT GTC ATC CTG GAG GTG AAT GAG GCT GTT CTG ACT GAG     2592
Glu Ile Lys Asn Val Ile Leu Glu Val Asn Glu Ala Val Leu Thr Glu
850                 855                 860

TCT ATG ATC CAG AAC CTC ATT AAG CAA ATG CCA GAG CCA GAG CAG TTA     2640
Ser Met Ile Gln Asn Leu Ile Lys Gln Met Pro Glu Pro Glu Gln Leu
865                 870                 875                 880

AAA ATG CTT TCT GAA CTG AAG GAT GAA TAT GAT GAC CTG GCT GAG TCA     2688
Lys Met Leu Ser Glu Leu Lys Asp Glu Tyr Asp Asp Leu Ala Glu Ser
                885                 890                 895

GAG CAG TTT GGC GTG GTG ATG GGC ACT GTG CCC CGA CTG CGG CCT CGC     2736
Glu Gln Phe Gly Val Val Met Gly Thr Val Pro Arg Leu Arg Pro Arg
            900                 905                 910
```

```
CTC AAT GCC ATT CTC TTC AAG CTA CAA TTC AGC GAG CAA GTG GAG AAT      2784
Leu Asn Ala Ile Leu Phe Lys Leu Gln Phe Ser Glu Gln Val Glu Asn
            915                 920                 925

ATC AAG CCA GAG ATT GTG TCT GTC ACT GCT GCA TGT GAG GAG TTA CGT      2832
Ile Lys Pro Glu Ile Val Ser Val Thr Ala Ala Cys Glu Glu Leu Arg
930                 935                 940

AAG AGT GAG AGC TTT TCC AAT CTC CTA GAG ATT ACC TTG CTT GTT GGA      2880
Lys Ser Glu Ser Phe Ser Asn Leu Leu Glu Ile Thr Leu Leu Val Gly
945                 950                 955                 960

AAT TAC ATG AAT GCT GGC TCC AGA AAT GCT GGT GCT TTT GGC TTC AAT      2928
Asn Tyr Met Asn Ala Gly Ser Arg Asn Ala Gly Ala Phe Gly Phe Asn
                965                 970                 975

ATC AGC TTC CTC TGT AAG CTT CGA GAC ACC AAG TCC ACA GAT CAG AAG      2976
Ile Ser Phe Leu Cys Lys Leu Arg Asp Thr Lys Ser Thr Asp Gln Lys
            980                 985                 990

ATG ACG TTG TTA CAC TTC TTG GCT GAG TTG TGT GAG AAT GAC TAT CCC      3024
Met Thr Leu Leu His Phe Leu Ala Glu Leu Cys Glu Asn Asp Tyr Pro
        995                 1000                1005

GAT GTC CTC AAG TTT CCA GAC GAG CTT GCC CAT GTG GAG AAA GCC AGC      3072
Asp Val Leu Lys Phe Pro Asp Glu Leu Ala His Val Glu Lys Ala Ser
    1010                1015                1020

CGA GTT TCT GCT GAA AAC TTG CAA AAG AAC CTA GAT CAG ATG AAG AAA      3120
Arg Val Ser Ala Glu Asn Leu Gln Lys Asn Leu Asp Gln Met Lys Lys
1025                1030                1035                1040

CAA ATT TCT GAT GTG GAA CGT GAT GTT CAG AAT TTC CCA GCT GCC ACA      3168
Gln Ile Ser Asp Val Glu Arg Asp Val Gln Asn Phe Pro Ala Ala Thr
                1045                1050                1055

GAT GAA AAA GAC AAG TTT GTT GAA AAA ATG ACC AGC TTT GTG AAG GAT      3216
Asp Glu Lys Asp Lys Phe Val Glu Lys Met Thr Ser Phe Val Lys Asp
            1060                1065                1070

GCA CAG GAA CAG TAT AAC AAG CTG CGG ATG ATG CAT TCT AAC ATG GAG      3264
Ala Gln Glu Gln Tyr Asn Lys Leu Arg Met Met His Ser Asn Met Glu
        1075                1080                1085

ACC CTC TAT AAG GAG CTG GGC GAG TAC TTC CTC TTT GAC CCC AAG AAG      3312
Thr Leu Tyr Lys Glu Leu Gly Glu Tyr Phe Leu Phe Asp Pro Lys Lys
    1090                1095                1100

TTG TCT GTT GAA GAA TTT TTC ATG GAT CTT CAC AAT TTT CGG AAT ATG      3360
Leu Ser Val Glu Glu Phe Phe Met Asp Leu His Asn Phe Arg Asn Met
1105                1110                1115                1120

TTT TTG CAA GCA GTC AAG GAG AAC CAG AAG CGG CGG AAG ACA GAA GAA      3408
Phe Leu Gln Ala Val Lys Glu Asn Gln Lys Arg Arg Lys Thr Glu Glu
                1125                1130                1135

AAG ATG AGG CGA GCA AAA CTA GCC AAG GAG AAG GCA GAG AAG GAG CGG      3456
Lys Met Arg Arg Ala Lys Leu Ala Lys Glu Lys Ala Glu Lys Glu Arg
            1140                1145                1150

CTA GAG AAG CAG CAG AAG AGA GAG CAA CTC ATA GAC ATG AAT GCA GAG      3504
Leu Glu Lys Gln Gln Lys Arg Glu Gln Leu Ile Asp Met Asn Ala Glu
        1155                1160                1165

GGC GAT GAG ACA GGT GTG ATG GAC AGT CTT CTA GAA GCC CTG CAG TCA      3552
Gly Asp Glu Thr Gly Val Met Asp Ser Leu Leu Glu Ala Leu Gln Ser
    1170                1175                1180

GGG GCA GCA TTC CGA CGG AAG AGA GGG CCC CGT CAA GCC AAC AGG AAG      3600
Gly Ala Ala Phe Arg Arg Lys Arg Gly Pro Arg Gln Ala Asn Arg Lys
1185                1190                1195                1200

GCC GGG TGT GCA GTC ACA TCT CTG CTA GCT TCG GAG CTG ACC AAG GAT      3648
Ala Gly Cys Ala Val Thr Ser Leu Leu Ala Ser Glu Leu Thr Lys Asp
                1205                1210                1215

GAT GCC ATG GCT GCT GTT CCT GCC AAG GTG TCC AAG AAC AGT GAG ACA      3696
Asp Ala Met Ala Ala Val Pro Ala Lys Val Ser Lys Asn Ser Glu Thr
```

```
                   1220           1225            1230
TTC CCC ACA ATC CTT GAG GAA GCC AAG GAG TTG GTT GGC CGT GCA AGC         3744
Phe Pro Thr Ile Leu Glu Glu Ala Lys Glu Leu Val Gly Arg Ala Ser
        1235            1240            1245

TAA                                                                     3747
```

(2) INFORMATION FOR SEQ ID NO:2:

(i) SEQUENCE CHARACTERISTICS:
        (A) LENGTH: 1248 amino acids
        (B) TYPE: amino acid
        (D) TOPOLOGY: linear (ii) MOLECULE TYPE: protein (xi) SEQUENCE DESCRIPTION: SEQ ID NO:2:

```
Met Glu Pro Pro Gly Gly Ser Leu Gly Pro Gly Arg Glu Thr Arg Asp
 1               5                  10                  15

Lys Lys Lys Gly Arg Ser Pro Asp Glu Leu Pro Ser Ala Gly Gly Asp
            20                  25                  30

Gly Gly Lys Ser Lys Phe Leu Glu Arg Phe Thr Ser Met Arg Ile
        35                  40                  45

Lys Lys Glu Lys Glu Lys Pro Asn Ser Ala His Arg Asn Ser Ser Ala
    50                  55                  60

Ser Tyr Gly Asp Asp Pro Thr Ala Gln Ser Leu Gln Asp Val Ser Asp
 65                  70                  75                  80

Glu Gln Val Leu Val Leu Phe Glu Gln Met Leu Leu Asp Met Asn Leu
                85                  90                  95

Asn Glu Glu Lys Gln Gln Pro Leu Arg Glu Lys Asp Ile Ile Ile Lys
            100                 105                 110

Arg Glu Met Val Ser Gln Tyr Leu Tyr Thr Ser Lys Ala Gly Met Ser
        115                 120                 125

Gln Lys Glu Ser Ser Lys Ser Ala Met Met Tyr Ile Gln Glu Leu Arg
    130                 135                 140

Ser Gly Leu Arg Asp Met Pro Leu Leu Ser Cys Leu Glu Ser Leu Arg
145                 150                 155                 160

Val Ser Leu Asn Asn Pro Val Ser Trp Val Gln Thr Phe Gly Ala
            165                 170                 175

Glu Gly Leu Ala Ser Leu Leu Asp Ile Leu Lys Arg Leu His Asp Glu
        180                 185                 190

Lys Glu Glu Thr Ala Gly Ser Tyr Asp Ser Arg Asn Lys His Glu Ile
    195                 200                 205

Ile Arg Cys Leu Lys Ala Phe Met Asn Asn Lys Phe Gly Ile Lys Thr
210                 215                 220

Met Leu Glu Thr Glu Glu Gly Ile Leu Leu Leu Val Arg Ala Met Asp
225                 230                 235                 240

Pro Ala Val Pro Asn Met Met Ile Asp Ala Ala Lys Leu Leu Ser Ala
            245                 250                 255

Leu Cys Ile Leu Pro Gln Pro Glu Asp Met Asn Glu Arg Val Leu Glu
        260                 265                 270

Ala Met Thr Glu Arg Ala Glu Met Asp Glu Val Glu Arg Phe Gln Pro
    275                 280                 285

Leu Leu Asp Gly Leu Lys Ser Gly Thr Thr Ile Ala Leu Lys Val Gly
    290                 295                 300

Cys Leu Gln Leu Ile Asn Ala Leu Ile Thr Pro Ala Glu Glu Leu Asp
305                 310                 315                 320
```

-continued

```
Phe Arg Val His Ile Arg Ser Glu Leu Met Arg Leu Gly Leu His Gln
            325                 330                 335

Val Leu Gln Asp Leu Arg Glu Ile Glu Asn Glu Asp Met Arg Val Gln
            340                 345                 350

Leu Asn Val Phe Asp Glu Gln Gly Glu Glu Asp Ser Tyr Asp Leu Lys
            355                 360                 365

Gly Arg Leu Asp Asp Ile Arg Met Glu Met Asp Phe Asn Glu Val
            370                 375                 380

Phe Gln Ile Leu Leu Asn Thr Val Lys Asp Ser Lys Ala Glu Pro His
385                 390                 395                 400

Phe Leu Ser Ile Leu Gln His Leu Leu Leu Val Arg Asn Asp Tyr Glu
            405                 410                 415

Ala Arg Pro Gln Tyr Tyr Lys Leu Ile Glu Glu Cys Ile Ser Gln Ile
            420                 425                 430

Val Leu His Lys Asn Gly Ala Asp Pro Asp Phe Lys Cys Arg His Leu
            435                 440                 445

Gln Ile Glu Ile Glu Gly Leu Ile Asp Gln Met Ile Asp Lys Thr Lys
450                 455                 460

Val Glu Lys Ser Glu Ala Lys Ala Ala Glu Leu Glu Lys Lys Leu Asp
465                 470                 475                 480

Ser Glu Leu Thr Ala Arg His Glu Leu Gln Val Glu Met Lys Lys Met
            485                 490                 495

Glu Ser Asp Phe Glu Gln Lys Leu Gln Asp Leu Gln Gly Glu Lys Asp
            500                 505                 510

Ala Leu His Ser Glu Lys Gln Gln Ile Ala Thr Glu Lys Gln Asp Leu
            515                 520                 525

Glu Ala Glu Val Ser Gln Leu Thr Gly Glu Val Ala Lys Leu Thr Lys
            530                 535                 540

Glu Leu Glu Asp Ala Lys Lys Glu Met Ala Ser Leu Ser Ala Ala Ala
545                 550                 555                 560

Ile Thr Val Pro Pro Ser Val Pro Ser Arg Ala Pro Val Pro Pro Ala
            565                 570                 575

Pro Pro Leu Pro Gly Asp Ser Gly Thr Ile Ile Pro Pro Pro Pro Ala
            580                 585                 590

Pro Gly Asp Ser Thr Thr Pro Pro Pro Pro Pro Pro Pro Pro Pro Pro
            595                 600                 605

Pro Pro Pro Leu Pro Gly Gly Thr Ala Ile Ser Pro Pro Pro Pro Leu
            610                 615                 620

Ser Gly Asp Ala Thr Ile Pro Pro Pro Pro Leu Pro Glu Gly Val
625                 630                 635                 640

Gly Ile Pro Ser Pro Ser Ser Leu Pro Gly Gly Thr Ala Ile Pro Pro
            645                 650                 655

Pro Pro Pro Leu Pro Gly Ser Ala Arg Ile Pro Pro Pro Pro Pro Pro
            660                 665                 670

Leu Pro Gly Ser Ala Gly Ile Pro Pro Pro Pro Leu Pro Gly
            675                 680                 685

Glu Ala Gly Met Pro Pro Pro Pro Pro Leu Pro Gly Gly Pro Gly
            690                 695                 700

Ile Pro Pro Pro Pro Phe Pro Gly Gly Pro Gly Ile Pro Pro Pro
705                 710                 715                 720

Pro Pro Gly Met Gly Met Pro Pro Pro Pro Phe Gly Phe Gly Val
            725                 730                 735
```

```
Pro Ala Ala Pro Val Leu Pro Phe Gly Leu Thr Pro Lys Lys Leu Tyr
            740                 745                 750
Lys Pro Glu Val Gln Leu Arg Arg Pro Asn Trp Ser Lys Leu Val Ala
        755                 760                 765
Glu Asp Leu Ser Gln Asp Cys Phe Trp Thr Lys Val Lys Glu Asp Arg
        770                 775                 780
Phe Glu Asn Asn Glu Leu Phe Ala Lys Leu Thr Leu Thr Phe Ser Ala
785                 790                 795                 800
Gln Thr Lys Thr Lys Lys Asp Gln Glu Gly Gly Glu Lys Lys Ser
                805                 810                 815
Val Gln Lys Lys Val Lys Glu Leu Lys Val Leu Asp Ser Lys Thr
                820                 825                 830
Ala Gln Asn Leu Ser Ile Phe Leu Gly Ser Phe Arg Met Pro Tyr Gln
            835                 840                 845
Glu Ile Lys Asn Val Ile Leu Glu Val Asn Glu Ala Val Leu Thr Glu
        850                 855                 860
Ser Met Ile Gln Asn Leu Ile Lys Gln Met Pro Glu Pro Glu Gln Leu
865                 870                 875                 880
Lys Met Leu Ser Glu Leu Lys Asp Glu Tyr Asp Leu Ala Glu Ser
                885                 890                 895
Glu Gln Phe Gly Val Val Met Gly Thr Val Pro Arg Leu Arg Pro Arg
            900                 905                 910
Leu Asn Ala Ile Leu Phe Lys Leu Gln Phe Ser Glu Gln Val Glu Asn
            915                 920                 925
Ile Lys Pro Glu Ile Val Ser Val Thr Ala Ala Cys Glu Glu Leu Arg
        930                 935                 940
Lys Ser Glu Ser Phe Ser Asn Leu Leu Glu Ile Thr Leu Leu Val Gly
945                 950                 955                 960
Asn Tyr Met Asn Ala Gly Ser Arg Asn Ala Gly Ala Phe Gly Phe Asn
                965                 970                 975
Ile Ser Phe Leu Cys Lys Leu Arg Asp Thr Lys Ser Thr Asp Gln Lys
            980                 985                 990
Met Thr Leu Leu His Phe Leu Ala Glu Leu Cys Glu Asn Asp Tyr Pro
        995                 1000                1005
Asp Val Leu Lys Phe Pro Asp Glu Leu Ala His Val Glu Lys Ala Ser
        1010                1015                1020
Arg Val Ser Ala Glu Asn Leu Gln Lys Asn Leu Asp Gln Met Lys Lys
1025                1030                1035                1040
Gln Ile Ser Asp Val Glu Arg Asp Val Gln Asn Phe Pro Ala Ala Thr
            1045                1050                1055
Asp Glu Lys Asp Lys Phe Val Glu Lys Met Thr Ser Phe Val Lys Asp
            1060                1065                1070
Ala Gln Glu Gln Tyr Asn Lys Leu Arg Met Met His Ser Asn Met Glu
        1075                1080                1085
Thr Leu Tyr Lys Glu Leu Gly Glu Tyr Phe Leu Phe Asp Pro Lys Lys
        1090                1095                1100
Leu Ser Val Glu Glu Phe Phe Met Asp Leu His Asn Phe Arg Asn Met
1105                1110                1115                1120
Phe Leu Gln Ala Val Lys Glu Asn Gln Lys Arg Arg Lys Thr Glu Glu
            1125                1130                1135
Lys Met Arg Arg Ala Lys Leu Ala Lys Glu Lys Ala Glu Lys Glu Arg
            1140                1145                1150
Leu Glu Lys Gln Gln Lys Arg Glu Gln Leu Ile Asp Met Asn Ala Glu
```

Gly Asp Glu Thr Gly Val Met Asp Ser Leu Leu Glu Ala Leu Gln Ser
    1170                1175                1180

Gly Ala Ala Phe Arg Arg Lys Arg Gly Pro Arg Gln Ala Asn Arg Lys
1185                1190                1195                1200

Ala Gly Cys Ala Val Thr Ser Leu Leu Ala Ser Glu Leu Thr Lys Asp
            1205                1210                1215

Asp Ala Met Ala Ala Val Pro Ala Lys Val Ser Lys Asn Ser Glu Thr
        1220                1225                1230

Phe Pro Thr Ile Leu Glu Glu Ala Lys Glu Leu Val Gly Arg Ala Ser
    1235                1240                1245

(2) INFORMATION FOR SEQ ID NO:3:

(i) SEQUENCE CHARACTERISTICS:
        (A) LENGTH: 4378 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:3:

```
GAAGGCTGCT GGGCGGCGGC GGTGGTTGCT GGCTCGGGGC AGCCGGGCGC GAGCGGCGTA      60

GACAAGGGGT CACTTGCCGG CGCTAATCAG GACATGGAGC CGTCCGGCGG GGGCCTGGGG     120

CCCGGCCGCG GTACCCGGGA CAAGAAGAAG GGTCGGAGCC CGGATGAGCT GCCTGCGACG     180

GGCGGCGACG GCGGCAAACA TAAGAAATTT CTGGAGAGAT TTACCAGCAT GAGGATTAAG     240

AAGGAGAAAG AAAAGCCCAA TTCTGCTCAT AGAAACTCCT CTGCATCGTA CGGAGATGAC     300

CCCACTGCTC AGTCATTGCA GGACATCTCA GACGAGCAAG TTCTTGTCCT CTTTGAGCAG     360

ATGCTGGTGG ATATGAACCT GAATGAGGAG AAGCAGCAGC CTTTGCGAGA AAGGACATT     420

GTCATCAAGA GGGAGATGGT GTCGCAATAT CTGCACACTT CCAAGGCTGG CATGAACCAG     480

AAAGAGAGCT CTAGGTCTGC CATGATGTAC ATCCAGGAGC TGAGGTCGGG CTTGCGGGAT     540

ATGCACCTGC TTAGCTGCCT TGAGTCCCTT CGAGTCTCTC TCAACAATAA CCCTGTCAGT     600

TGGGTGCAGA CATTTGGTGC TGAGGGCCTA GCCTCCTTAT TGGACATCCT CAAACGACTC     660

CATGATGAGA AGAGGAGAC TTCTGGAAAC TACGACAGCC GAAACCAGCA TGAGATTATC     720

CGCTGTTTGA AGGCTTTCAT GAACAACAAG TTTGGAATCA AAACTATGTT GGAGACGGAA     780

GAAGGAATCC TACTGCTGGT CAGAGCCATG GATCCTGCTG TTCCCAATAT GATGATTGAT     840

GCAGCAAAGC TGCTGTCTGC CCTCTGTATC CTGCCGCAGC CGGAGGACAT GAATGAACGA     900

GTTCTAGAGG CAATGACAGA GAGAGCTGAA ATGGATGAGG TCGAACGCTT CCAGCCACTT     960

CTGGACGGAT TAAAAAGTGG GACCTCTATT GCCCTCAAAG TGGGATGCCT ACAGCTCATC    1020

AATGCTCTCA TCACTCCAGC TGAGGAACTG GACTTCCGAG TTCACATCCG AAGTGAGCTG    1080

ATGCGCCTGG GGCTGCATCA GGTGTTGCAG GAGCTTCGAG AGATTGAAAA TGAAGATATG    1140

AAAGTACAGC TGTGCGTGTT TGATGAACAA GGGGATGAAG ATTTCTTTGA TCTGAAGGGA    1200

CGGCTGGATG ATATCCGCAT GGAGATGGAT GACTTTGGTG AAGTTTTTCA GATTATTTTA    1260

AACACAGTGA AGATTCAAAA GCAGAGCCA CACTTCCTGT CTATCTTGCA GCATCTCCTG    1320

TTGGTCCGAA ATGATTATGA AGCCAGGCCA CAGTACTATA AACTGATTGA AGAATGTGTT    1380

TCTCAGATAG TTCTACACAA AAATGGAACT GATCCTGACT TCAAGTGCCG ACACCTGCAG    1440

ATTGATATTG AGAGATTGGT TGATCAAATG ATTGATAAAA CAAAGGTGGA AAAATCTGAG    1500
```

-continued

```
GCCAAAGCTA CAGAGCTGGA AAAAAGTTG GATTCAGAAT TAACAGCGCG GCACGAGTTA      1560

CAAGTAGAAA TGAAAAAGAT GGAAAATGAC TTTGAGCAGA AACTTCAGGA TCTTCAAGGA      1620

GAAAAGGATG CCTTGGATTC TGAAAAGCAG CAGATCACTG CACAGAAACA AGACCTGGAG      1680

GCAGAGGTGT CCAAGCTGAC AGGAGAGGTT GCCAAGCTGT CAAAAGAACT AGAAGATGCC      1740

AAGAATGAAA TGGCTTCTCT CTCTGCTGTG GTTGTTGCAC CTTCTGTTTC TAGCAGTGCT      1800

GCTGTTCCCC CTGCCCCTCC TCTGCCTGGT GACTCTGGCA CTGTTATTCC ACCTCCCCCA      1860

CCCCCACCTC CTCTTCCTGG AGGTGTGGTC CCACCATCCC CTCCTCTGCC TCCAGGTACT      1920

TGTATCCCTC CACCTCCTCC TTTACCTGGA GGTGCTTGTA TACCCCCTCC CCCCCAGTTG      1980

CCTGGCAGTG CTGCCATCCC TCCACCTCCT CCTCTACCTG GAGTTGCTTC CATCCCCCCA      2040

CCTCCCCCTT TGCCTGGGGC TACTGCCATC CCCCCACCTC CCCCTTTGCC TGGGGCTACT      2100

GCCATCCCCC CACCTCCCCC TTTGCCTGGA GGTACAGGTA TACCACCACC ACCTCCTCCT      2160

TTGCCTGGAA GTGTTGGCGT TCCCCCACCC CCTCCCTTGC CTGGAGGACC AGGACTGCCT      2220

CCTCCCCCCC CCCCTTTTCC TGGAGCACCT GGCATTCCTC CACCTCCACC TGGTATGGGC      2280

GTGCCTCCAC CTCCCCCCTT TGGATTTGGG GTTCCTGCGG CCCCAGTTCT GCCATTTGGA      2340

TTAACCCCCA AAAAGTTTA TAAGCCAGAG GTGCAGCTCC GGAGGCCAAA CTGGTCCAAG       2400

TTTGTGGCTG AGGACCTTTC CCAGGACTGC TTCTGGACAA AGGTGAAGGA GGACCGCTTT      2460

GAGAACAATG AACTTTTTGC CAAACTTACC CTTGCCTTCT CCGCCCAGAC CAAGACTTCT      2520

AAAGCCAAGA AGGATCAAGA AGGTGGAGAA GAAAAGAAAT CTGTTCAAAA GAAGAAAGTA      2580

AAAGAGCTGA AGTGCTGGA TTCAAAGACA GCGCAGAATC TCTCAATCTT TTTGGGTTCA       2640

TTCCGCATGC CCTATCAAGA GATAAAGAAC GTTATCCTGG AGGTGAATGA GGCTGTTCTC      2700

ACAGAGTCTA TGATCCAGAA CCTCATTAAA CAGATGCCAG AGCCAGAGCA GCTAAAGATG      2760

CTCTCTGAAC TGAAGGAGGA GTACGATGAT CTGGCTGAGT CAGAGCAGTT TGGTGTGGTG      2820

ATGGGCACAG TGCCCCGCCT TCGGCCTCGC CTCAACGCCA TCCTCTTCAA GCTACAGTTC      2880

AGTGAGCAAG TTGAGAACAT CAAGCCAGAG ATCGTGTCTG TCACCGCCGC ATGCGAAGAG      2940

CTGCGTAAGA GTGAGAACTT CTCCAGCCTC CTGGAGCTCA CACTGCTGGT CGGAAACTAT      3000

ATGAATGCGG GCTCCAGGAA TGCTGGTGCT TTCGGCTTCA ATATCAGCTT CCTTTGTAAG      3060

CTTCGAGACA CCAAGTCTGC AGATCAGAAG ATGACTCTGT TGCATTTCTT GGCTGAGTTA      3120

TGTGAGAATG ACCACCCCGA AGTCCTCAAG TTTCCTGATG AGCTTGCCCA TGTAGAGAAA      3180

GCCAGCAGAG TCTCTGCTGA GAACCTGCAG AAGAGCTTAG ATCAGATGAA GAAGCAGATT      3240

GCGGACGTGG AGCGCGATGT TCAGAATTTC CCAGCTGCCA CTGACGAGAA GGACAAGTTT      3300

GTTGAGAAGA TGACCAGCTT TGTGAAGGAT GCACAGGAAC AGTATAACAA ACTACGGATG      3360

ATGCACTCCA ACATGGAGAC CCTCTATAAG GAGCTAGGTG ACTACTTCGT CTTTGACCCT      3420

AAGAAGTTGT CTGTAGAGGA ATTCTTTATG GATCTGCACA ACTTTAGGAA TATGTTTTTG      3480

CAAGCAGTCA AGGAAAACCA GAAGCGCCGG GAAACAGAAG AAAAGATGCG GAGAGCAAAA      3540

TTAGCCAAGG AGAAGGCAGA AAAAGAGCGA CTGGAGAAGC AGCAGAAGCG CGAGCAGCTC      3600

ATCGACATGA ACGCAGAGGG GGATGAGACA GGTGTGATGG ACAGTCTTCT AGAAGCTCTG      3660

CAGTCAGGGG CAGCATTCCG ACGGAAGAGA GGGCCCCGGC AGGTCAACAG GAAGGCTGGG      3720

TGTGCAGTCA CATCTCTGCT AGCCTCGGAG CTGACCAAGG ATGATGCCAT GGCTCCTGGT      3780

CCTGTTAAGG TACCCAAGAA AAGTGAAGGA GTCCCCACAA TCCTGGAAGA AGCCAAGGAG      3840
```

```
CTGGTTGGCC GTGCAAGCTA AGCTGGGCTT TATGGCCATT GCTGCTCCTA GGCGAAGCCC    3900

AGACTGTCGA CCTGCAGCAT GGGCCTAAAT GGTCAAGGAG ATAGTGGCCA CTCCACCACC    3960

TGACCCTGTC TTTCTGTCTG GCCTGCTGCT CTCTGAACAC CACATACAGC TTCAGCTGCC    4020

TGGAGGCCAA AAGGAAGGGG CAGTGTAGGA GTGGCCTGAG CCCAGCCCAG CCAGCCCTGG    4080

CTGTTGTATT ACCAAAGCAG GGTCCGTGTT TGCTGCCTTA ACCCTGTCTC CTCTATGTTA    4140

CCCAGAGGTC CTGGTCTCAG ACAGAACCCA GCCTGCTTTC TCAGCCCCAC TCTCTAGTGG    4200

GCCTTCCCTA GGTCAATCTT GCTGCATTTG TGCTTTTCTT TTGTGGTTTC TCTGGCCCTG    4260

AGAATAGCAT GGGACTTGTG AACCTTTGGG CTAGGTCTTT TCACTGCTGT CACCTCTGCT    4320

TTTCCTCCTG GCAATTATTT ATTACTAGTG CTGTGGCATT GGGAGCTGCT TCTGCAAA     4378
```

(2) INFORMATION FOR SEQ ID NO:4:

(i) SEQUENCE CHARACTERISTICS:
        (A) LENGTH: 1255 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

```
Met Glu Pro Ser Gly Gly Leu Gly Pro Gly Arg Gly Thr Arg Asp
 1               5                  10                  15

Lys Lys Lys Gly Arg Ser Pro Asp Glu Leu Pro Ala Thr Gly Asp
                20                  25                  30

Gly Gly Lys His Lys Lys Phe Leu Glu Arg Phe Thr Ser Met Arg
            35                  40                  45

Lys Lys Glu Lys Glu Lys Pro Asn Ser Ala His Arg Asn Ser Ser
        50                  55                  60

Ser Tyr Gly Asp Asp Pro Thr Ala Gln Ser Leu Gln Asp Ile Ser Asp
 65                  70                  75                  80

Glu Gln Val Leu Val Leu Phe Glu Gln Met Leu Val Asp Met Asn Leu
                85                  90                  95

Asn Glu Glu Lys Gln Gln Pro Leu Arg Glu Lys Asp Ile Val Ile Lys
                100                 105                 110

Arg Glu Met Val Ser Gln Tyr Leu His Thr Ser Lys Ala Gly Met Asn
            115                 120                 125

Gln Lys Glu Ser Ser Arg Ser Ala Met Met Tyr Ile Gln Glu Leu Arg
        130                 135                 140

Ser Gly Leu Arg Asp Met His Leu Leu Ser Cys Leu Glu Ser Leu Arg
145                 150                 155                 160

Val Ser Leu Asn Asn Asn Pro Val Ser Trp Val Gln Thr Phe Gly Ala
                165                 170                 175

Glu Gly Leu Ala Ser Leu Leu Asp Ile Leu Lys Arg Leu His Asp Glu
            180                 185                 190

Lys Glu Glu Thr Ser Gly Asn Tyr Asp Ser Arg Asn Gln His Glu Ile
        195                 200                 205

Ile Arg Cys Leu Lys Ala Phe Met Asn Asn Lys Phe Gly Ile Lys Thr
    210                 215                 220

Met Leu Glu Thr Glu Glu Gly Ile Leu Leu Leu Val Arg Ala Met Asp
225                 230                 235                 240

Pro Ala Val Pro Asn Met Met Ile Asp Ala Ala Lys Leu Leu Ser Ala
                245                 250                 255
```

```
Leu Cys Ile Leu Pro Gln Pro Glu Asp Met Asn Glu Arg Val Leu Glu
            260                 265                 270

Ala Met Thr Glu Arg Ala Glu Met Asp Glu Val Glu Arg Phe Gln Pro
            275                 280                 285

Leu Leu Asp Gly Leu Lys Ser Gly Thr Ser Ile Ala Leu Lys Val Gly
            290                 295                 300

Cys Leu Gln Leu Ile Asn Ala Leu Ile Thr Pro Ala Glu Glu Leu Asp
305                 310                 315                 320

Phe Arg Val His Ile Arg Ser Glu Leu Met Arg Leu Gly Leu His Gln
                325                 330                 335

Val Leu Gln Glu Leu Arg Glu Ile Glu Asn Glu Asp Met Lys Val Gln
            340                 345                 350

Leu Cys Val Phe Asp Glu Gln Gly Asp Glu Asp Phe Phe Asp Leu Lys
            355                 360                 365

Gly Arg Leu Asp Asp Ile Arg Met Glu Met Asp Asp Phe Gly Glu Val
        370                 375                 380

Phe Gln Ile Ile Leu Asn Thr Val Lys Asp Ser Lys Ala Glu Pro His
385                 390                 395                 400

Phe Leu Ser Ile Leu Gln His Leu Leu Leu Val Arg Asn Asp Tyr Glu
                405                 410                 415

Ala Arg Pro Gln Tyr Tyr Lys Leu Ile Glu Glu Cys Val Ser Gln Ile
            420                 425                 430

Val Leu His Lys Asn Gly Thr Asp Pro Asp Phe Lys Cys Arg His Leu
            435                 440                 445

Gln Ile Asp Ile Glu Arg Leu Val Asp Gln Met Ile Asp Lys Thr Lys
        450                 455                 460

Val Glu Lys Ser Glu Ala Lys Ala Thr Glu Leu Glu Lys Lys Leu Asp
465                 470                 475                 480

Ser Glu Leu Thr Ala Arg His Glu Leu Gln Val Glu Met Lys Lys Met
                485                 490                 495

Glu Asn Asp Phe Glu Gln Lys Leu Gln Asp Leu Gln Gly Glu Lys Asp
            500                 505                 510

Ala Leu Asp Ser Glu Lys Gln Gln Ile Thr Ala Gln Lys Gln Asp Leu
            515                 520                 525

Glu Ala Glu Val Ser Lys Leu Thr Gly Glu Val Ala Lys Leu Ser Lys
            530                 535                 540

Glu Leu Glu Asp Ala Lys Asn Glu Met Ala Ser Leu Ser Ala Val Val
545                 550                 555                 560

Val Ala Pro Ser Val Ser Ser Ala Ala Val Pro Ala Pro Pro
                565                 570                 575

Leu Pro Gly Asp Ser Gly Thr Val Ile Pro Pro Pro Pro Pro
            580                 585                 590

Pro Leu Pro Gly Val Val Pro Pro Ser Pro Pro Leu Pro Pro Gly
            595                 600                 605

Thr Cys Ile Pro Pro Pro Pro Leu Pro Gly Gly Ala Cys Ile Pro
            610                 615                 620

Pro Pro Pro Gln Leu Pro Gly Ser Ala Ala Ile Pro Pro Pro Pro Pro
625                 630                 635                 640

Leu Pro Gly Val Ala Ser Ile Pro Pro Pro Pro Leu Pro Gly Ala
                645                 650                 655

Thr Ala Ile Pro Pro Pro Pro Leu Pro Gly Ala Thr Ala Ile Pro
            660                 665                 670

Pro Pro Pro Pro Leu Pro Gly Gly Thr Gly Ile Pro Pro Pro Pro
```

-continued

```
                675                 680                 685
Pro Leu Pro Gly Ser Val Gly Val Pro Pro Pro Pro Leu Pro Gly
            690                 695                 700

Gly Pro Gly Leu Pro Pro Pro Pro Pro Phe Pro Gly Ala Pro Gly
705                 710                 715                 720

Ile Pro Pro Pro Pro Gly Met Gly Val Pro Pro Pro Pro Pro Phe
                725                 730                 735

Gly Phe Gly Val Pro Ala Ala Pro Val Leu Pro Phe Gly Leu Thr Pro
            740                 745                 750

Lys Lys Val Tyr Lys Pro Glu Val Gln Leu Arg Arg Pro Asn Trp Ser
            755                 760                 765

Lys Phe Val Ala Glu Asp Leu Ser Gln Asp Cys Phe Trp Thr Lys Val
770                 775                 780

Lys Glu Asp Arg Phe Glu Asn Asn Glu Leu Phe Ala Lys Leu Thr Leu
785                 790                 795                 800

Ala Phe Ser Ala Gln Thr Lys Thr Ser Lys Ala Lys Lys Asp Gln Glu
                805                 810                 815

Gly Gly Glu Glu Lys Lys Ser Val Gln Lys Lys Val Lys Glu Leu
            820                 825                 830

Lys Val Leu Asp Ser Lys Thr Ala Gln Asn Leu Ser Ile Phe Leu Gly
            835                 840                 845

Ser Phe Arg Met Pro Tyr Gln Glu Ile Lys Asn Val Ile Leu Glu Val
850                 855                 860

Asn Glu Ala Val Leu Thr Glu Ser Met Ile Gln Asn Leu Ile Lys Gln
865                 870                 875                 880

Met Pro Glu Pro Glu Gln Leu Lys Met Leu Ser Glu Leu Lys Glu Glu
                885                 890                 895

Tyr Asp Asp Leu Ala Glu Ser Glu Gln Phe Gly Val Val Met Gly Thr
            900                 905                 910

Val Pro Arg Leu Arg Pro Arg Leu Asn Ala Ile Leu Phe Lys Leu Gln
            915                 920                 925

Phe Ser Glu Gln Val Glu Asn Ile Lys Pro Glu Ile Val Ser Val Thr
930                 935                 940

Ala Ala Cys Glu Glu Leu Arg Lys Ser Glu Asn Phe Ser Ser Leu Leu
945                 950                 955                 960

Glu Leu Thr Leu Leu Val Gly Asn Tyr Met Asn Ala Gly Ser Arg Asn
                965                 970                 975

Ala Gly Ala Phe Gly Phe Asn Ile Ser Phe Leu Cys Lys Leu Arg Asp
            980                 985                 990

Thr Lys Ser Ala Asp Gln Lys Met Thr Leu Leu His Phe Leu Ala Glu
            995                 1000                1005

Leu Cys Glu Asn Asp His Pro Glu Val Leu Lys Phe Pro Asp Glu Leu
    1010                1015                1020

Ala His Val Glu Lys Ala Ser Arg Val Ser Ala Glu Asn Leu Gln Lys
1025                1030                1035                1040

Ser Leu Asp Gln Met Lys Lys Gln Ile Ala Asp Val Glu Arg Asp Val
                1045                1050                1055

Gln Asn Phe Pro Ala Ala Thr Asp Glu Lys Asp Lys Phe Val Glu Lys
            1060                1065                1070

Met Thr Ser Phe Val Lys Asp Ala Gln Glu Gln Tyr Asn Lys Leu Arg
            1075                1080                1085

Met Met His Ser Asn Met Glu Thr Leu Tyr Lys Glu Leu Gly Asp Tyr
    1090                1095                1100
```

```
Phe Val Phe Asp Pro Lys Lys Leu Ser Val Glu Glu Phe Phe Met Asp
1105                1110                1115                1120

Leu His Asn Phe Arg Asn Met Phe Leu Gln Ala Val Lys Glu Asn Gln
            1125                1130                1135

Lys Arg Arg Glu Thr Glu Glu Lys Met Arg Arg Ala Lys Leu Ala Lys
                1140                1145                1150

Glu Lys Ala Glu Lys Glu Arg Leu Glu Lys Gln Gln Lys Arg Glu Gln
            1155                1160                1165

Leu Ile Asp Met Asn Ala Glu Gly Asp Glu Thr Gly Val Met Asp Ser
        1170                1175                1180

Leu Leu Glu Ala Leu Gln Ser Gly Ala Ala Phe Arg Arg Lys Arg Gly
1185                1190                1195                1200

Pro Arg Gln Val Asn Arg Lys Ala Gly Cys Ala Val Thr Ser Leu Leu
                1205                1210                1215

Ala Ser Glu Leu Thr Lys Asp Asp Ala Met Ala Pro Gly Pro Val Lys
            1220                1225                1230

Val Pro Lys Lys Ser Glu Gly Val Pro Thr Ile Leu Glu Glu Ala Lys
        1235                1240                1245

Glu Leu Val Gly Arg Ala Ser
    1250                1255

(2) INFORMATION FOR SEQ ID NO:5:

(i) SEQUENCE CHARACTERISTICS:
        (A) LENGTH: 1641 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:5:

GCACGAGCCT TAACGAAGAG AAAAAAGCTC CTTTACGAAA CAAAGACTTT ACCACCAAAC      60

GTGAGATGGT TGTCCAGTAT ATTTCTGCCA CTGCCAAATC TGGTGGGCTG AAAAACAGCA    120

AACATGAATG CACCCTGTCT TCACAAGAAT ATGTTCATGA ATTACGATCG GGTATATCAG    180

ATGAGAAACT TCTTAATTGC CTAGAATCCC TCAGGGTTTC TTTAACCAGC AATCCGGTCA    240

GCTGGGTTAA CAACTTTGGC CATGAAGGTC TTGGACTCTT ATTGGATGAG CTGGAAAAGC    300

TTCTGGACAA AAAACAGCAA GAAAATATTG ACAAGAAGAA TCAGTATAAA CTTATTCAAT    360

GCCTCAAAGC ATTTATGAAT AATAAGTTTG GCTTACAAAG GATTCTAGGA GATGAAAGAA    420

GTCTTTTGCT ATTGGCAAGA GCAATTGACC CCAAACAACC AACATGATG ACTGAAATAG     480

TAAAAATACT TCGGCAATT GCATTGTTGG AGAAGAGACA CTCTAGATAA ACTTTTACGG     540

GGCTATAACA CAGCAGCACG AAGAAATAAC ACGGAACGAC TTTCACCACT TGTGGACCGT    600

TTACAAATCA NGAATCCTTG CATTACAGGT GGCTGCATGC ACTTTATAAT GCCCATGTAC    660

TTCTCCTTAG AGCTGCATTT CGACACTTTA CGGATGATTC CTCGTCACGA CTAAACACAG    720

TACAGATGAT AGCAAAGAGA TGTGAGCTGA CATCACTTGA CGTATTTGTA ACACAAAAAT    780

GCCTACCGCA TTTCACCCTC TTCTGCAATT GNGAAAGTAA GCGGTCAAAA TCCCGGTTGG    840

GTTAAACAAT CCGTAAAATC GAGGTTTTAT TCGCGATTAA ACAACCGTT CGATTATGCC     900

GACTTTGGAG GAAAATTGAG ATTCTAAAAT GTCCTAAGAA TGTGAACACG TTGAAGTGCA    960

AGCAAGTTCA GCCCAAGTTG TCAGAGCACC CTGCATCATG GAACAACAAT TGTTCATCTG   1020

GAAGTGACAT CAAGAAATTC CGCCAAGCAG AAATCAACAC GATAGGTGTG TGAAAAGATG   1080
```

-continued

```
ACCAGTTTAC AAAGACTGCC CGAGAACTGT ATGAAAAACT GTCCAACCAT GCACAACAAC    1140

ATGATGAAGC TCTATGAGAA TCTTGGAGAA TACTTCATTT TTGACTCAAA GACAGTGAGC    1200

ATAGAAGAGT TCTTTGGTGA TCTCAACAAC TTCCGAACTT TGTTTTTGGA AGCAGTGAGA    1260

GAAAACAATA TGAGAAGAGA AATGGAAGAG AAGACCAGGA GGGCAAAACT TGCAAAAGAG    1320

AAAGCTGAAC AAGAAAAGTT AGAACGCCAG AAGAAAAAGA AACAACTCAT TGATATAAAC    1380

AAAGAGGGTG ATGAGACTGG TGTGATGGAT AATCTTCTAG AAGCCCTACA ATCAGGTGCA    1440

GCATTCAGAG ACCGTCGAAA GCGGATTCCA AGGAATCCAG TGGTAAATCA TCCCTGTGCA    1500

ACAAGGGCTA ATCCAAGATC AGCTACATAA ACGGCCTGAG TGCTGTTTTA AACAGGATTG    1560

GGTGATGGTA CAACATGACT TTTTAAGATA ATCAAGTAGT AAAAGTTTCT AGTGGAAACA    1620

TGAAAAAAAA AAAAAAAAA A                                               1641
```

(2) INFORMATION FOR SEQ ID NO:6:

(i) SEQUENCE CHARACTERISTICS:
      (A) LENGTH: 362 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:6:

```
Ser Leu Asn Glu Glu Lys Lys Ala Pro Leu Arg Asn Lys Asp Phe Thr
1               5                  10                  15

Thr Lys Arg Glu Met Val Val Gln Tyr Ile Ala Thr Ala Lys Gly Gly
            20                  25                  30

Leu Ser Lys His Glu Cys Thr Leu Ser Ser Gln Glu Tyr Val His Glu
        35                  40                  45

Leu Arg Ser Gly Ile Ser Asp Glu Lys Leu Leu Asn Cys Leu Glu Ser
    50                  55                  60

Leu Arg Val Ser Leu Thr Ser Asn Pro Val Ser Trp Val Asn Asn Phe
65                  70                  75                  80

Gly His Glu Gly Leu Gly Leu Leu Leu Asp Glu Leu Glu Lys Leu Leu
                85                  90                  95

Asp Lys Lys Gln Gln Glu Asn Ile Asp Lys Lys Asn Gln Tyr Lys Leu
            100                 105                 110

Ile Gln Cys Leu Lys Ala Phe Met Asn Lys Phe Gly Leu Gln Arg
        115                 120                 125

Ile Leu Gly Asp Glu Arg Ser Leu Leu Leu Ala Arg Ala Ile Asp
    130                 135                 140

Pro Lys Gln Pro Asn Met Met Thr Glu Ile Val Lys Ile Leu Ser Ala
145                 150                 155                 160

Ile Ala Leu Leu Glu Lys Arg His Xaa Asp Phe Gly Gly Lys Leu Arg
                165                 170                 175

Phe Asn Val Leu Arg Met Thr Arg Ala Ser Lys Phe Ser Pro Ser Cys
            180                 185                 190

Gln Ser Thr Leu His His Gly Thr Thr Ile Val His Leu Glu Val Thr
        195                 200                 205

Ser Arg Asn Ser Ala Lys Gln Lys Ser Thr Arg Val Cys Glu Lys Met
    210                 215                 220

Thr Ser Leu Gln Arg Leu Pro Glu Asn Cys Met Lys Asn Cys Pro Thr
225                 230                 235                 240
```

```
Met His Asn Asn Met Met Lys Leu Tyr Glu Asn Leu Gly Glu Tyr Phe
                245                 250                 255

Ile Phe Asp Ser Lys Thr Val Ser Ile Glu Glu Phe Phe Gly Asp Leu
            260                 265                 270

Asn Asn Phe Arg Thr Leu Phe Leu Glu Ala Val Arg Glu Asn Asn Met
        275                 280                 285

Arg Arg Glu Met Glu Lys Thr Arg Arg Ala Lys Leu Ala Lys Glu
    290                 295                 300

Lys Ala Glu Gln Glu Lys Leu Glu Arg Gln Lys Lys Lys Gln Leu
305                 310                 315                 320

Ile Asp Ile Asn Lys Glu Gly Asp Glu Thr Gly Val Met Asp Asn Leu
                325                 330                 335

Leu Glu Ala Leu Gln Ser Gly Ala Ala Phe Arg Arg Lys Arg Ile Pro
                340                 345                 350

Arg Asn Pro Val Val Asn His Pro Cys Ala
        355                 360
```

(2) INFORMATION FOR SEQ ID NO:7:

(i) SEQUENCE CHARACTERISTICS:
        (A) LENGTH: 23 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:7:

AGTCATCCAT CTCCATGCGA ATG        23

(2) INFORMATION FOR SEQ ID NO:8:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:8:

ATGCGAATGT CATCCAGCCG TC        22

(2) INFORMATION FOR SEQ ID NO:9:

(i) SEQUENCE CHARACTERISTICS:
        (A) LENGTH: 18 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:9:

TTGCGGGATA TGCCTCTG        18

(2) INFORMATION FOR SEQ ID NO:10:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:10:

GGTTGTTGTT GAGAGACACA C                                          21

(2) INFORMATION FOR SEQ ID NO:11:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:11:

TGTGGGAGAG GGGAAATCAA G                                          21

(2) INFORMATION FOR SEQ ID NO:12:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:12:

TTGCTCTTTA GCCGCAGACT GG                                         22

(2) INFORMATION FOR SEQ ID NO:13:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:13:

CGGCGGAAGA CAGAAGAAAA G                                          21

(2) INFORMATION FOR SEQ ID NO:14:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:14:

TAGCAGAGAT GTGACTGCAC ACCC                                       24